(12) United States Patent
Shuttleworth et al.

(10) Patent No.: US 10,377,764 B2
(45) Date of Patent: Aug. 13, 2019

(54) TRICYCLIC HETEROCYCLIC COMPOUNDS AS PHOSPHOINOSITIDE 3-KINASE INHIBITORS

(71) Applicant: Karus Therapeutics Limited, Oxfordshire (GB)

(72) Inventors: Stephen Joseph Shuttleworth, Oxfordshire (GB); Franck Alexandre Silva, Oxfordshire (GB); Alexander Richard Liam Cecil, Oxfordshire (GB); Alice Elizabeth Gatland, Oxfordshire (GB); Daniel John Finnemore, Oxfordshire (GB)

(73) Assignee: Karus Therapeutics Limited, Oxfordshire (GB)

( * ) Notice: Subject to any disclaimer, the term of this patent is extended or adjusted under 35 U.S.C. 154(b) by 0 days.

(21) Appl. No.: 15/753,361

(22) PCT Filed: Aug. 19, 2016

(86) PCT No.: PCT/GB2016/052578
§ 371 (c)(1),
(2) Date: Feb. 19, 2018

(87) PCT Pub. No.: WO2017/029519
PCT Pub. Date: Feb. 23, 2017

(65) Prior Publication Data
US 2018/0244686 A1    Aug. 30, 2018

(30) Foreign Application Priority Data

Aug. 19, 2015  (GB) .................................. 1514751.5

(51) Int. Cl.
C07D 491/147    (2006.01)
C07D 495/14     (2006.01)
C07D 519/00     (2006.01)

(52) U.S. Cl.
CPC ....... *C07D 491/147* (2013.01); *C07D 495/14* (2013.01); *C07D 519/00* (2013.01)

(58) Field of Classification Search
CPC ........................... C07D 491/147; C07D 495/14
See application file for complete search history.

(56) References Cited

U.S. PATENT DOCUMENTS

| | | | |
|---|---|---|---|
| 3,491,092 A | 1/1970 | Grigat et al. | |
| 4,017,500 A | 4/1977 | Mayer et al. | |
| 5,703,075 A | 12/1997 | Gammill et al. | |
| 7,361,662 B2 | 4/2008 | Rault et al. | |
| 8,981,087 B2 | 3/2015 | Shuttleworth et al. | |
| 9,200,007 B2 | 12/2015 | Shuttleworth et al. | |
| 9,266,879 B2 | 2/2016 | Shuttleworth et al. | |
| 9,580,442 B2 | 2/2017 | Shuttleworth et al. | |
| 9,663,487 B2 | 5/2017 | Shuttleworth et al. | |
| 9,938,290 B2 | 4/2018 | Shuttleworth et al. | |
| 9,981,987 B2 | 5/2018 | Shuttleworth et al. | |
| 10,035,785 B2 | 7/2018 | Shuttleworth et al. | |
| 2002/0151544 A1 | 10/2002 | Hayakawa et al. | |
| 2007/0135466 A1 | 6/2007 | Ledeboer et al. | |
| 2011/0201608 A1 | 8/2011 | Hoffmann et al. | |
| 2013/0109688 A1 | 5/2013 | Shuttleworth et al. | |
| 2015/0080395 A1 | 3/2015 | Shuttleworth et al. | |
| 2016/0108057 A1 | 4/2016 | Shuttleworth et al. | |
| 2016/0347771 A1 | 12/2016 | Shuttleworth et al. | |
| 2018/0235974 A1 | 8/2018 | Shuttleworth et al. | |
| 2018/0243313 A1 | 8/2018 | Shuttleworth et al. | |
| 2018/0243317 A1 | 8/2018 | Shuttleworth et al. | |
| 2018/0244685 A1 | 8/2018 | Shuttleworth et al. | |

FOREIGN PATENT DOCUMENTS

| | | |
|---|---|---|
| EP | 1277738 A1 | 1/2003 |
| EP | 1724267 A1 | 11/2006 |
| WO | WO-01/83456 A1 | 11/2001 |
| WO | WO-02/02551 A1 | 1/2002 |

(Continued)

OTHER PUBLICATIONS

Alvarez-Rua et al., "Multiple Hydrogen Bonds and Tautomerism in Naphthyridine Derivatives", New J. Chem. 28, 700-07 (2004).
Ameriks et al., "Small Molecule Inhibitors of Phosphoinositide 3-Kinase (PI3K) δ and γ", Current Topics in Medicinal Chemistry, 2009, vol. 9, No. 8, pp. 738-753.
Baldev Singh et al., "Novel cAMP PDE III Inhibitors: 1,6-Naphthyridin-2(18)-ones", Journal of Medicinal Chemistry, American Chemical Society, 35(26): 5858-4865, Jan. 1, 1992, New York.
CAS Registry Nos. 1214438-02-4 and 1214393-37-9 (Mar. 25, 2010).
D.A. Kovalskiy et al., "Synthesis of 7-(3-piperidyl)[1,6]naphthyridine and 7-(4-piperidyl)[1,6]naphthyridine", Chemistry of Heterocyclic Compounds, 45(9): 1053-1057, Nov. 24, 2009.
Database Chemcats [Online], Chemical Abstracts Service, Apr. 22, 2011, Columbus, Ohio.

(Continued)

*Primary Examiner* — Bruck Kifle
(74) *Attorney, Agent, or Firm* — Goodwin Procter LLP

(57) ABSTRACT

The invention relates to a compound of formula I: (I) or a pharmaceutically acceptable salt thereof, wherein each $R^3$ is independently selected from H, halo, fluorinated $C_1$-$C_{10}$ alkyl, —I—$C_1$-$C_{10}$ alkyl, —NH—$C_1$-$C_{10}$ alkyl, —S—$C_1$-$C_{10}$ alkyl, —O-fluorinated $C_1$-$C_{10}$ alkyl, —NH-acyl, —NH—C(O)—NH-alkyl, —C—(O)—NH-alkyl, with the proviso that at least one of $R^3$ is not H.

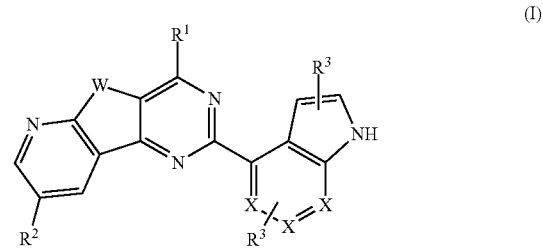

2 Claims, No Drawings

(56) References Cited

FOREIGN PATENT DOCUMENTS

| WO | WO-02/085400 A1 | 10/2002 |
|---|---|---|
| WO | WO-2004/006846 A2 | 1/2004 |
| WO | WO-2004/043956 A1 | 5/2004 |
| WO | WO-2006/046035 A1 | 5/2006 |
| WO | WO-2006/127587 A1 | 11/2006 |
| WO | WO-2007/084667 A2 | 7/2007 |
| WO | WO-2007/122410 A1 | 11/2007 |
| WO | WO-2007/127183 A1 | 11/2007 |
| WO | WO-2008/064018 A1 | 5/2008 |
| WO | WO-2008/094992 A2 | 8/2008 |
| WO | WO-2008/121257 A1 | 10/2008 |
| WO | WO-2008/145688 A2 | 12/2008 |
| WO | WO-2008/150827 A1 | 12/2008 |
| WO | WO-2010/015520 A1 | 2/2010 |
| WO | WO-2010/037765 A2 | 4/2010 |
| WO | WO-2010/052569 A2 | 5/2010 |
| WO | WO-2011/012883 A1 | 2/2011 |
| WO | WO-2011/021038 A1 | 2/2011 |
| WO | WO-2011/079231 A1 | 6/2011 |
| WO | WO-2011/135351 A1 | 11/2011 |
| WO | WO-2013/014448 A1 | 1/2013 |
| WO | WO-2013/017480 A1 | 2/2013 |
| WO | WO-2013/132270 A1 | 9/2013 |
| WO | WO-2014/081718 A1 | 5/2014 |
| WO | WO-2014/181137 A1 | 11/2014 |
| WO | WO-2014/210354 A1 | 12/2014 |
| WO | WO-2015/054355 A1 | 4/2015 |
| WO | WO-2015/121657 A1 | 8/2015 |
| WO | WO-2017/029514 A1 | 2/2017 |
| WO | WO-2017/029517 A1 | 2/2017 |
| WO | WO-2017/029518 A1 | 2/2017 |
| WO | WO-2017/029519 A1 | 2/2017 |
| WO | WO-2017/029521 A1 | 2/2017 |

OTHER PUBLICATIONS

Erik L. Meredith et al., "Identification of Orally Available Naphthyridine Protein Kinase D Inhibitors", Journal of Medicinal Chemistry, 53(15): 5400-5421, Aug. 12, 2010.
Fabbro et al. Pharmacology & Therapeutics 93, 79-98, 2002.
Golub et al., Science, 286, 531-537, 1999.
Hayakawa, et al., "Synthesis and Biological Evaluation of Pyrido[3',2':4,5]furo[3,2-d]pyrimidine Derivatives as Novel PI3 Kinase p110α Inhibitors" Bioorganic & Medicinal Chemistry Letters, 2007, vol. 17, pp. 2438-2442.
Hollebecque A et al., (2014), 'A Phase Ib Trial of LY2584702 Tosylate, a p70 S6 Inhibitor, in Combination with Erlotinib or Everolimus in Patients with Solid Tumours,' Eur J Cancer, 50(5):876-84.
International Preliminary Report on Patentability and Written Opinion of the International Searching Authority for PCT/GB2010/051221 dated Jan. 31, 2012 (7 pages).
International Preliminary Report on Patentability and Written Opinion of the International Searching Authority for PCT/GB2010/051370 dated Feb. 21, 2012 (6 pages).
International Preliminary Report on Patentability and Written Opinion of the International Searching Authority for PCT/GB2011/050824 dated Nov. 6, 2012 (7 pages).
International Preliminary Report on Patentability and Written Opinion of the International Searching Authority for PCT/GB2013/050583 dated Sep. 9, 2014 (6 pages).
International Search Report of the International Searching Authority for PCT/GB2010/051221 dated Oct. 7, 2010 (4 pages).
International Search Report of the International Searching Authority for PCT/GB2010/051370 dated Nov. 9, 2010 (4 pages).
International Search Report of the International Searching Authority for PCT/GB2011/050824 dated Jul. 12, 2011 (5 pages).
International Search Report of the International Searching Authority for PCT/GB2013/050583 dated May 6, 2013 (4 pages).
Lin L et al., (2014), 'Dual Targeting of Glioblastoma Multiforme with a Proteasome Inhibitor (Velcade) and a Phosphatidylinositol 3-Kinase Inhibitor (ZSTK474),' Int J Oncol, 44(2):557-62.
Mass, R. D., Int. J. Radiation Oncology Bio. Phys. vol. 58 (3): 932-940, 2004.
Notification of the Transmittal of the International Search Report and the Written Opinion of the International Searching Authority, or the Declaration, (form ISA/220), International Application No. PCT/GB2016/052575, dated Nov. 9, 2016 (13 pages).
Notification of the Transmittal of the International Search Report and the Written Opinion of the International Searching Authority, or the Declaration, (form ISA/220), International Application No. PCT/GB2016/052577, dated Nov. 9, 2016 (10 pages).
Notification of the Transmittal of the International Search Report and the Written Opinion of the International Searching Authority, or the Declaration, (form ISA/220), International Application No. PCT/GB2016/052578, dated Oct. 25, 2016 (12 pages).
Notification of the Transmittal of the International Search Report and the Written Opinion of the International Searching Authority, or the Declaration, (form ISA/220), International Application No. PCT/GB2016/052581, dated Oct. 24, 2016 (13 pages).
Schröder E et al., 'Arzneimittel Chemie Passage,' Arzneimittelchemie Grundlagen Nerven, Muskeln und Gewebe [Pharmaceutical Chemistry I: Basic, Nerves, Muscles and Tissues], (1st Ed, 1976), Thieme Georg Verla, Stuttgart DE (Publ) pp. 30-33 and Table 8 XP002186820.
Tao J et al., (2013), 'Combined Treatment of BTK and PI3K Inhibitors Synergistically Disrupts BCR-Signaling, Overcomes Microenvironment-Mediated Survival and Drug Resistance in Mantle Cell Lymphoma,' Proceedings of the 104th Annual Meeting of the American Association for Cancer Research, Apr. 6-10, 2013, Washington, D.C. Philadelphia PA, AACR Abstract #4944, Oasis, Chicago, IL (Publ) (2 pages) [retrieved on Jul. 16, 2014 at <http://wwwabstractsonline.com/Plan/ViewAbstract.aspx?Key=605>...] (Abstract).
Verheijen et al., "Phosphatidylinositol 3-kinase (PI3K) inhibitors as anticancer drugs", Drugs of the Future, 2007, vol. 32, No. 6, pp. 537-547.
Yamada T et al., (2013) 'A Novel HDAC Inhibitor OBP-801 and a PI3K Inhibitor LY294002 Synergistically Induce Apoptosis via the Suppression of Survivin and XIAP in Renal Cell Carcinoma,' Int J Oncol, 43(4):1080-6.
Zhong H et al., (2013) 'Synergistic Effects of Concurrent Blockade of PI3K and MEK Pathways in Pancreatic Cancer Preclinical Models,' PLoS One, 8(10):e77243.
Zhou W et al., (2009) 'Novel Mutant-Selective EGFR Kinase Inhibitors Against EGFR T790M, Nature, 462(7276):1070-4 [NIH Public Access Version].
Cohen et al., Current Opinion in Chemical Biology, 3, 459-465, 1999.
International Preliminary Report on Patentability and Written Opinion of the International Searching Authority for PCT/GB2015/050396 dated Aug. 16, 2016 (6 pages).
International Search Report of the International Searching Authority for PCT/GB2015/050396 dated Mar. 25, 2015 (3 pages).
Somei et al., "Boronation-Thallation, A New Approach to the Synthesis of Indoles Having Aryl and/or a Heteroaryl Substituent at the 4-Position." Chem. Pharm. Bull. 1986, 34, 3971-3.
Annex to Form PCT/ISA/206 Communication relating to the results of the partial international search for International Application No. PCT/GB2016/052571 dated Nov. 9, 2016 (4 pages).
Saifuddin, M. et al., "Water-Accelerated Cationic pi-(7-endo) cyclisation: Application to Indole-Based Peri-Annulated Polyheterocycles." European Journal of Organic Chemistry, 2010, 26, 5108-5117.
Written Opinion of the International Searching Authority for PCT/GB2016/052571 dated Feb. 23, 2017 (9 pages).
International Search Report of the International Searching Authority for PCT/GB2016/052571 dated Feb. 23, 2017 (6 pages).

TRICYCLIC HETEROCYCLIC COMPOUNDS AS PHOSPHOINOSITIDE 3-KINASE INHIBITORS

CROSS-REFERENCE TO RELATED APPLICATIONS

This application is the national stage application of International Patent Application No. PCT/GB2016/052578, filed Aug. 19, 2016, which claims the benefit of and priority to Great Britain Patent Application No. 1514751.5, filed Aug. 19, 2015, the contents of each of which are hereby incorporated by reference in their entirety.

FIELD OF THE INVENTION

The present invention relates to novel compounds which act as inhibitors of the class IA phosphoinositide 3-kinase enzymes, PI3K-p110β and PI3K-p110δ, for the treatment of cancer, immune and inflammatory diseases.

BACKGROUND OF THE INVENTION

The phosphoinositide 3-kinases (PI3Ks) constitute a family of lipid kinases involved in the regulation of a network of signal transduction pathways that control a range of cellular processes. PI3Ks are classified into three distinct subfamilies, named class I, II, and III based upon their substrate specificities. Class IA PI3Ks possess a p110α, p110β, or p110δ catalytic subunit complexed with one of three regulatory subunits, p85α, p85β or p55δ. Class IA PI3Ks are activated by receptor tyrosine kinases, antigen receptors, G-protein coupled receptors (GPCRs), and cytokine receptors. The class IA PI3Ks primarily generate phosphatidylinositol-3,4,5-triphosphate (PI(3,4,5)P$_3$), a second messenger that activates the downstream target AKT. The consequences of biological activation of AKT include tumour cell progression, proliferation, survival and growth, and there is significant evidence suggesting that the PI3K/AKT pathway is dysregulated in many human cancers. Additionally, PI3K activity has been implicated in endocrinology, cardiovascular disease, immune disorders and inflammation. It has been established that PI3K-p110δ plays a critical role in the recruitment and activation of immune and inflammatory cells. PI3K-p110δ is also upregulated in a number of human tumours and plays a key role in tumour cell proliferation and survival.

Compounds which are able to modulate p110δ and p110β activity have important therapeutic potential in cancer and immune and inflammatory disorders.

WO 2011/021038 describes compounds which act as inhibitors of PI3K-p110δ.

WO2010/052569 also discloses 6,5,6 PI3K inhibitors.

SUMMARY OF THE INVENTION

The present invention relates to a selection of compounds having increased activity and/or bioavailability over the compounds described in WO 2011/021038. It is expected that compounds of the present invention will be more potent at inhibiting p110δ than those disclosed in WO 2011/021038. Without wishing to be bound by theory, this is believed to be owing to the provision of the substituent on the indole, preferably wherein the substituent bears a halogen atom.

With respect to the 6,5,6-compounds disclosed in WO2010/052569, the compounds of the invention have a substituent in the meta-position, which is preferred.

Therefore, the present invention is a compound of Formula I:

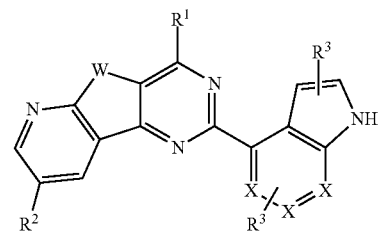

or a pharmaceutically acceptable salt thereof, wherein:

W is O, N—H, N—($C_1$-$C_{10}$ alkyl) or S;

each X is independently selected from CH or N;

$R^1$ is a 5 to 7-membered saturated or unsaturated, optionally substituted heterocycle containing at least 1 heteroatom selected from N or O;

$R^2$ is $(LQ)_vY$, with the proviso that $R^2$ is not H;

each L is independently selected from the group consisting of a direct bond, $C_1$-$C_{10}$ alkylene, $C_2$-$C_{10}$ alkenylene, $C_2$-$C_{10}$ alkynylene, arylene and $C_3$-$C_{10}$ cycloalkylene;

each Q is independently a direct bond, heteroarylene, a heterocycle linker, —O—, —$NR^6$—, —C(O)—, —C(O)$NR^6$—, —$SO_2$—, —$SO_2$—$NR^6$—, —NH—C(O)—$NR^6$—, —NH—$SO_2$—$NR^6$, halogen, —C(halogen)$_a$($R^6_{(2-a)}$)—, —$NR^4R^5$—, —C(O)$NR^4R^5$, where $R^4$ and $R^5$ together with the nitrogen to which they are attached form a 4 to 10-membered heterocycle linker;

v is from 0 to 5;

Y is H, $C_1$-$C_{10}$ alkyl, $C_2$-$C_{10}$ alkenyl, $C_2$-$C_{10}$ alkenyl, $C_2$-$C_{10}$ alkynyl, aryl, $C_3$-$C_{10}$ cycloalkyl, heterocycle, heteroaryl, —$OR^6$, —$N(R^6)_2$, —C(O)$R^6$, —C(O)$OR^6$, —C(O)$N(R^6)_2$, —$N(R^6)_2$, —$SO_2$—$R^6$, —$SO_2$—$N(R^6)_2$, —NH—C(O)—$N(R^6)_2$, —NH—$SO_2$—$N(R^6)_2$, halogen, —C(halogen)$_b R^6_{(3-b)}$, —CN, —$NR^4R^5$—, —C(O)$NR^4R^5$, where $R^4$ and $R^5$ together with the nitrogen to which they are attached form a 4- to 10-membered heterocycle;

b is from 1 to 3;

a is 1 or 2;

each $R^6$ is independently selected from H, $C_{1-10}$ alkyl, aryl or heteroaryl; and each $R^3$ is independently selected from H, halo, fluorinated $C_1$-$C_{10}$ alkyl, —O—$C_1$-$C_{10}$ alkyl, —NH—$C_1$-$C_{10}$ alkyl, —S—$C_1$-$C_{10}$ alkyl, —O-fluorinated $C_1$-$C_{10}$ alkyl, —NH-acyl, —NH—C(O)—NH-alkyl, —C—(O)—NH-alkyl, with the proviso that at least one of $R^3$ is not H.

DESCRIPTION OF THE PREFERRED EMBODIMENTS

Definitions

As used herein, "alkyl" means a $C_1$-$C_{10}$ alkyl group, which can be linear or branched. Preferably, it is a $C_1$-$C_6$ alkyl moiety. More preferably, it is a $C_1$-$C_4$ alkyl moiety. Examples include methyl, ethyl, n-propyl and t-butyl. It may be divalent (i.e. alkylene), e.g. propylene.

As used herein, "alkenyl" means a $C_2$-$C_{10}$ alkenyl group. Preferably, it is a $C_2$-$C_6$ alkenyl group. More preferably, it is a $C_2$-$C_4$ alkenyl group. The alkenyl radicals may be mono- or di-saturated, more preferably monosaturated. Examples include vinyl, allyl, 1-propenyl, isopropenyl and 1-butenyl. It may be divalent (i.e. alkenylene), e.g. propenylene.

used herein, "alkynyl" is a $C_2$-$C_{10}$ alkynyl group which can be linear or branched. Preferably, it is a $C_2$-$C_4$ alkynyl group or moiety. It may be divalent.

Each of the $C_1$-$C_{10}$ alkyl, $C_2$-$C_{10}$ alkenyl and $C_2$-$C_{10}$ alkynyl groups may be optionally substituted with each other, i.e. $C_1$-$C_{10}$ alkyl optionally substituted with $C_2$-$C_{10}$ alkenyl. They may also be optionally substituted with aryl, cycloalkyl (preferably $C_3$-$C_{10}$), aryl or heteroaryl. They may also be substituted with halogen (e.g. F, Cl), $NH_2$, $NO_2$ or hydroxyl. Preferably, they may be substituted with up to 10 halogen atoms or more preferably up to 5 halogens. For example, they may be substituted by 1, 2, 3, 4 or 5 halogen atoms. Preferably, the halogen is fluorine. For example, they may be substituted with $CF_3$, $CHF_2$, $CH_2CF_3$, $CH_2CHF_2$ or $CF_2CF_3$. For example, $C_1$-$C_{10}$ alkyl may be $CF_3$, $CHF_2$, $CH_2CF_3$, $CH_2CHF_2$ or $CF_2CF_3$.

As used herein, "fluorinated alkyl" means a fluorinated $C_1$-$C_{10}$ alkyl, which can be linear or branched. The term "fluorinated $C_1$-$C_{10}$ alkyl" means $C_1$-$C_{10}$ alkyl that is partially or fully fluorinated. Preferably, it is a $C_1$-$C_6$ fluorinated alkyl moiety. More preferably, it is a $C_1$-$C_4$ fluorinated alkyl moiety. For example, "fluorinated $C_1$-$C_{10}$ alkyl" may be $CF_3$, $CHF_2$, $CH_2CF_3$, $CH_2CHF_2$ or $CF_2CF_3$.

As used herein, "aryl" means a monocyclic, bicyclic, or tricyclic monovalent or divalent (as appropriate) aromatic radical, such as phenyl, biphenyl, naphthyl, anthracenyl, which can be optionally substituted with up to five substituents preferably selected from the group of $C_1$-$C_6$ alkyl, hydroxy, $C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, "heteroaryl" means a monocyclic, bicyclic or tricyclic monovalent or divalent (as appropriate) aromatic radical containing up to four heteroatoms selected from oxygen, nitrogen and sulfur, such as thiazolyl, isothiazolyl, tetrazolyl, imidazolyl, oxazolyl, isoxazolyl, thienyl, pyrazolyl, pyridinyl, pyrazinyl, pyrimidinyl, indolyl, quinolyl, isoquinolyl, triazolyl, thiadiazolyl, oxadiazolyl, said radical being optionally substituted with up to three substituents preferably selected from the group of $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo, nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Amino means —$NH_2$.

As used herein, the term "heterocycle" or "heterocycloalkyl" is a mono- or di-valent carbocyclic radical containing up to 4 heteroatoms selected from oxygen, nitrogen and sulfur. It should contain from 4-12 ring atoms in total, preferably 4-10. Preferably, it contains one or two heteroatoms. Preferably, at least one of the heteroatoms is nitrogen. It may be monocyclic or bicyclic. If it is bicyclic, it may be fused, spirocyclic or bridged. It is preferably saturated. Examples of heterocycles are piperidine, piperazine, thiomorpholine, azetidine or morpholine.

The heterocyclic ring may be mono- or di-unsaturated, but preferably it is saturated. The radical may be optionally substituted with up to three substituents independently selected from $C_1$-$C_6$ alkyl, hydroxy, $C_1$-$C_3$ hydroxyalkyl, $C_1$-$C_3$ alkoxy, $C_1$-$C_3$ haloalkoxy, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, halo e.g. F, nitro, cyano, carboxy, $C_1$-$C_3$-haloalkyl e.g. $CF_3$, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

In summary, each of the groups defined above, i.e., alkyl, alkenyl, alkynyl, aryl, heteroaryl, heterocycle, heterocycloalkyl, may be optionally substituted with up to three substituents (preferably one) preferably selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

Alternatively, each of the groups defined above, i.e., alkyl, alkenyl, alkynyl, aryl, heteroaryl, heterocycle, heterocycloalkyl, may be optionally substitured by $R_x$, wherein $R_x$ is selected from the group consisting of $C_1$-$C_6$ alkyl, hydroxy, $C_1$-$C_3$ hydroxyalkyl, $C_1$-$C_3$ alkoxy, $C_1$-$C_3$ haloalkoxy, fluoro $C_1$-$C_3$ alkyl, amino, $C_1$-$C_3$ mono alkylamino, $C_1$-$C_3$ bis alkylamino, $C_1$-$C_3$ acylamino, $C_1$-$C_3$ aminoalkyl, mono ($C_1$-$C_3$ alkyl) amino $C_1$-$C_3$ alkyl, bis ($C_1$-$C_3$ alkyl) amino $C_1$-$C_3$ alkyl, $C_1$-$C_3$-acylamino, $C_1$-$C_3$ alkyl sulfonylamino, acyl, halo (e.g. fluoro), nitro, cyano, trifluoromethyl, carboxy, $C_1$-$C_3$ alkoxycarbonyl, aminocarbonyl, mono $C_1$-$C_3$ alkyl aminocarbonyl, bis $C_1$-$C_3$ alkyl aminocarbonyl, —$SO_3H$, $C_1$-$C_3$ alkylsulfonyl, aminosulfonyl, mono $C_1$-$C_3$ alkyl aminosulfonyl and bis $C_1$-$C_3$-alkyl aminosulfonyl.

As used herein, the above groups can be followed by the suffix -ene. This means that the group is divalent, i.e. a linker group.

As used herein, the term "fused" is intended to take its usual meaning within the art of organic chemistry. Fused systems, for example fused bicyclic systems, are those in which two rings share two and only two atoms.

As used herein, the term "bridged" is intended to take its usual meaning within the art of organic chemistry. Bridged compounds are compounds which contain interlocking rings. According to the invention, the atoms of the bridged non-aromatic group which form the bridgehead is either a tertiary carbon atom (when the remaining atom is hydrogen) or a quaternary carbon atom (when the remaining atom is not hydrogen). The bridge can be considered to be a chain of atoms (for example, alkyl) or a single atom (for example, O, S, N, C) connecting two bridgeheads.

As used herein, the term "spirocyclic" is intended to take its usual meaning within the art of organic chemistry. For example, a spirocyclic compound is a bicycle whose rings are attached though just one atom (known as a spiroatom).

The rings may be different in size, the same size. Preferably, according to the invention, the two rings which are joined via the same atom are non-aromatic heterocycles, preferably heterocycloalkyls. For example, the spirocyclic non-aromatic group of Formula I may be a bicycle wherein both rings are heterocycloalkyl and are attached through the same atom, preferably a carbon atom.

Preferred Groups of the Invention

Preferably, $R^1$ is represented by any of the following structures:

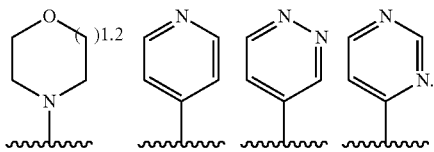

Most preferably, $R^1$ is morpholine.

In a preferred embodiment of the invention, W is oxygen or sulfur, preferably oxygen.

Preferably X is CH.

Preferably, v is 1.

Preferably, at least one $R^3$ is halo, fluorinated $C_1$-$C_{10}$ alkyl, —O-fluorinated $C_1$-$C_{10}$ alkyl. Most preferably, at least one $R^3$ is F or $CF_3$. In other words, it is preferred that one $R^3$ is F or $CF_3$ and the other is H.

For the avoidance of doubt, the $R^3$ substituents may be on any suitable position on the 6,5-system.

Preferably, the 6,5-ring system in Formula I is a substituted indole. In other words, X is CH.

Preferably, Q is a direct bond.

More preferably, $R^2$ is LY, wherein each L is a direct bond, $C_1$-$C_{10}$ alkylene, $C_2$-$C_{10}$ alkenylene or $C_2$-$C_{10}$ alkynylene or $C_1$-$C_{10}$; and Y is an optionally substituted heterocycle, preferably wherein said heterocycle contains one or two heteroatoms.

Alternatively, $R^2$ is LY, wherein each L is a direct bond, $C_1$-$C_{10}$ alkylene, $C_2$-$C_{10}$ alkenylene or $C_2$-$C_{10}$ alkynylene or $C_1$-$C_{10}$; and Y is an optionally substituted fused, bridged or spirocyclic non-aromatic heterocycle containing up to 4 heteroatoms selected from N or O, and comprising 4 to 12 atoms in total.

Preferably, $R^2$ is L-het-Q-Y, wherein het is a 4-7 monocyclic saturated heterocycle and Q, L and Y are as defined in any preceding claim. More preferably, L is a direct bond or $C_1$-$C_{10}$ alkylene.

More preferably, when $R^2$ is L-het-Q-Y, het is a 4-membered monocyclic saturated ring.

Preferably, Q is N or O and/or when Y is H or $C_1$ to $C_6$ alkyl.

Preferably, L is $C_1$-$C_{10}$ alkylene, preferably methylene.

Preferably, Y contains one or two heteroatoms, preferably two heteroatoms. More preferably, at least one of the heteroatoms is nitrogen and Y is bonded to L through the nitrogen atom, as depicted in the preferable Y groups below:

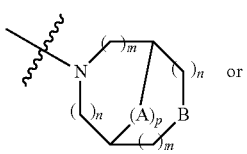

Formula A

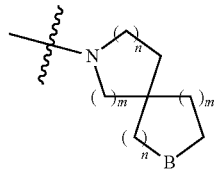

Formula B wherein:
A is selected from O, S, $NR^7$ or optionally substituted $C_1$-$C_3$ alkylene, $C_2$-$C_3$ alkenylene or $C_2$-$C_3$ alkynylene;
B is $NR^7$, O or $CH_2$,
wherein $R^7$ is H or optionally substituted $C_1$-$C_{10}$ alkyl, $C_2$-$C_{10}$ alkenyl, $C_2$-$C_{10}$ alkynyl or $C_1$-$C_3$ halofluoroalkyl;
p is selected from 0, 1 or 2;
each m is independently selected from 0, 1 or 2; and
each n is independently selected from 1, 2 or 3.
Preferably, A is O or $C_1$-$C_3$ alkylene, most preferably methylene.
Preferably, B is O or $CH_2$, most preferably O.
When $R^7$ is present, it is preferably H, $C_1$-$C_3$ alkyl or $C_1$-$C_3$ halofluoroalkyl. More preferably, $R^7$ is H.
Preferably, each m and n is selected so as to form 4- 5-, 6- or 7-membered nitrogen containing heterocycloalkyl groups. Preferably, p is 1. In particular, when A is O, S or $NR^7$, p is 1.
Preferably, when Y is Formula A, m is 0 and n is 1.
Y is preferably bicyclic, more preferably bridged bicyclic or spirocyclic bicyclic.
Even more preferably, Y is selected from a Y group as exemplified in any one of the exemplified compounds.

In another embodiment, provided herein are compounds represented by: In another embodiment, provided herein are compounds represented by:

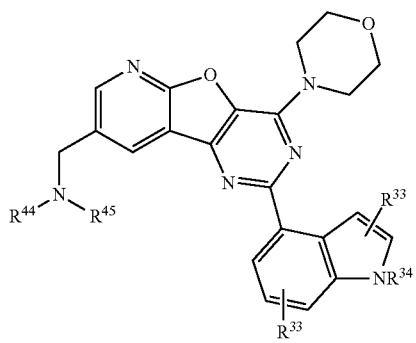

and pharmaceutically acceptable salts thereof, wherein:
$R^{33}$ is independently selected for each occurrence from the group consisting of H, halogen, cyano, $C_{1-6}$alkyl and —O—$C_{1-6}$alkyl (wherein $C_{1-6}$alkyl for each occurrence is substituted by one, two or three halogens, for example fluorine);
$R^{34}$ is selected from H or $C_{1-3}$alkyl (substituted by a one, two or three substituents; wherein at least one of $R^{33}$ or $R^{34}$ is not H;
$R^{44}$ and $R^{45}$, when taken together with the nitrogen to which they are attached form 4-6 membered heterocyclic ring, optionally substituted by one or two substituents each selected from the group consisting of: halogen (e.g., fluorine), $C_{1-6}$alkyl (optionally substituted by one two or three —OH or F), and $C_{1-6}$alkoxy (optionally substituted by one two or three —OH or F); or $R^{44}$ and $R^{45}$, taken together with the nitrogen to which they are attached, form a 7-10 membered bicyclic spirocycle or bridged heterocycle each having an additional heteroatom selected from O, S, or $NR^{55}$, wherein $R^{55}$ is H or $C_{1-3}$alkyl (optionally substituted by one two or three —OH or F) or $R^{44}$ is selected from the group consisting of H, $C_{1-6}$alkyl or $C_{3-6}$cycloalkyl and $R^{45}$ is selected from the group consisting of $C_{1-6}$alkyl or $C_{3-6}$cycloalkyl.

For example, $R^{44}$ and $R^{45}$, when taken together with the nitrogen to which they are attached form a 7-8 membered bicyclic bridged heterocycle represented by:

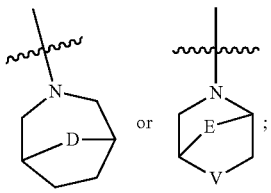

wherein D is O, S or $NR^{55}$; E is O or $(CH_2)_r$, wherein r is 1 or 2, and V is O or $NR^{55}$, wherein $R^{55}$ is H or $C_{1-3}$alkyl.

In another exemplary embodiment, $R^{44}$ and $R^{45}$, when taken together with the nitrogen to which they are attached form a 7-10 membered spirocycle having one additional heteroatom selected from O or $NR^{55}$, wherein $R^{55}$ is H or $C_{1-3}$alkyl.

For example, provided herein are compounds represented by:

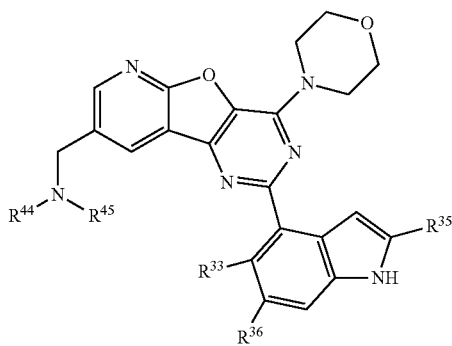

and pharmaceutically acceptable salts thereof, wherein R44 and R45 are defined above and wherein $R^{33}$, $R^{36}$, and $R^{35}$ are each independently selected from H, $CF_3$ and F, and wherein at least one of $R^{33}$, $R^{36}$, and $R^{35}$ is not H.

A pharmaceutical composition of the invention typically contains up to 85 wt % of a compound of the invention. More typically, it contains up to 50 wt % of a compound of the invention. Preferred pharmaceutical compositions are sterile and pyrogen-free. Further, the pharmaceutical compositions provided by the invention typically contain a compound of the invention which is a substantially pure optical isomer. Preferably, the pharmaceutical composition comprises a pharmaceutically acceptable salt form of a compound of the invention. For example, contemplated herein is a pharmaceutically acceptable composition comprising a disclosed compound and a pharmaceutically acceptable excipient.

As used herein, a pharmaceutically acceptable salt is a salt with a pharmaceutically acceptable acid or base. Pharmaceutically acceptable acids include both inorganic acids such as hydrochloric, sulfuric, phosphoric, diphosphoric, hydrobromic or nitric acid and organic acids such as citric, fumaric, maleic, malic, ascorbic, succinic, tartaric, benzoic, acetic, methanesulfonic, ethanesulfonic, salicylic, stearic, benzenesulfonic or p-toluenesulfonic acid. Pharmaceutically acceptable bases include alkali metal (e.g. sodium or potassium) and alkali earth metal (e.g. calcium or magnesium) hydroxides and organic bases such as alkyl amines, aryl amines or heterocyclic amines.

For the avoidance of doubt, the present invention also embraces prodrugs which react in vivo to give a compound of the present invention.

The compounds of the invention may be prepared by synthetic routes that will be apparent to those skilled in the art, e.g. based on the Examples.

The compounds of the invention and compositions comprising them may be administered in a variety of dosage forms. In one embodiment, a pharmaceutical composition comprising a compound of the invention may be formulated in a format suitable for oral, rectal, parenteral, intranasal or transdermal administration or administration by inhalation or by suppository. Typical routes of administration are parenteral, intranasal or transdermal administration or administration by inhalation.

The compounds of the invention can be administered orally, for example as tablets, troches, lozenges, aqueous or oily suspensions, dispersible powders or granules. Preferred pharmaceutical compositions of the invention are compositions suitable for oral administration, for example tablets and capsules.

The compounds of the invention may also be administered parenterally, whether subcutaneously, intravenously, intramuscularly, intrasternally, transdermally or by infusion techniques. The compounds may also be administered as suppositories.

The compounds of the invention may also be administered by inhalation. An advantage of inhaled medications is their direct delivery to the area of rich blood supply in comparison to many medications taken by oral route. Thus, the absorption is very rapid as the alveoli have an enormous surface area and rich blood supply and first pass metabolism is bypassed. A further advantage may be to treat diseases of the pulmonary system, such that delivering drugs by inhalation delivers them to the proximity of the cells which are required to be treated.

The present invention also provides an inhalation device containing such a pharmaceutical composition. Typically said device is a metered dose inhaler (MDI), which contains a pharmaceutically acceptable chemical propellant to push the medication out of the inhaler.

The compounds of the invention may also be administered by intranasal administration. The nasal cavity's highly permeable tissue is very receptive to medication and absorbs it quickly and efficiently, more so than drugs in tablet form. Nasal drug delivery is less painful and invasive than injections, generating less anxiety among patients. By this method absorption is very rapid and first pass metabolism is usually bypassed, thus reducing inter-patient variability. Further, the present invention also provides an intranasal device containing such a pharmaceutical composition.

The compounds of the invention may also be administered by transdermal administration. The present invention therefore also provides a transdermal patch containing a compound of the invention.

The compounds of the invention may also be administered by sublingual administration. The present invention therefore also provides a sub-lingual tablet comprising a compound of the invention.

A compound of the invention may also be formulated with an agent which reduces degradation of the substance by processes other than the normal metabolism of the patient, such as anti-bacterial agents, or inhibitors of protease enzymes which might be the present in the patient or in commensural or parasite organisms living on or within the patient, and which are capable of degrading the compound.

Liquid dispersions for oral administration may be syrups, emulsions and suspensions.

Suspensions and emulsions may contain as carrier, for example a natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g. sterile water, olive oil, ethyl oleate, glycols, e.g. propylene glycol, and if desired, a suitable amount of lidocaine hydrochloride.

Solutions for injection or infusion may contain as carrier, for example, sterile water or preferably they may be in the form of sterile, aqueous, isotonic saline solutions.

The compounds of the present invention can be used in both the treatment and prevention of cancer and can be used in a monotherapy or in a combination therapy. When used in a combination therapy, the compounds of the present invention are typically used together with small chemical compounds such as platinum complexes, anti-metabolites, DNA topoisomerase inhibitors, radiation, antibody-based therapies (for example herceptin and rituximab), anti-cancer vaccination, gene therapy, cellular therapies, hormone therapies or cytokine therapy.

In one embodiment of the invention a compound of the invention is used in combination with another chemotherapeutic or antineoplastic agent in the treatment of a cancer. Examples of such other chemotherapeutic or antineoplastic agents include platinum complexes including cisplatin and carboplatin, mitoxantrone, vinca alkaloids for example vincristine and vinblastine, anthracycline antibiotics for example daunorubicin and doxorubicin, alkylating agents for example chlorambucil and melphalan, taxanes for example paclitaxel, antifolates for example methotrexate and tomudex, epipodophyllotoxins for example etoposide, camptothecins for example irinotecan and its active metabolite SN38 and DNA methylation inhibitors for example the DNA methylation inhibitors disclosed in WO02/085400.

According to the invention, therefore, products are provided which contain a compound of the invention and another chemotherapeutic or antineoplastic agent as a combined preparation for simultaneous, separate or sequential use in alleviating a cancer. Also provided according to the invention is the use of compound of the invention in the manufacture of a medicament for use in the alleviation of cancer by coadministration with another chemotherapeutic or antineoplastic agent. The compound of the invention and the said other agent may be administrated in any order. In both these cases the compound of the invention and the other agent may be administered together or, if separately, in any order as determined by a physician.

The PI3K inhibitors of the present invention may also be used to treat abnormal cell proliferation due to insults to body tissue during surgery in a patient. These insults may arise as a result of a variety of surgical procedures such as joint surgery, bowel surgery, and cheloid scarring. Diseases that produce fibrotic tissue that may be treated using the PI3K inhibitors of the present invention include emphysema. Repetitive motion disorders that may be treated using the present invention include carpal tunnel syndrome. An example of a cell proliferative disorder that may be treated using the invention is a bone tumour.

Proliferative responses associated with organ transplantation that may be treated using PI3K inhibitors of the invention include proliferative responses contributing to potential organ rejections or associated complications. Specifically, these proliferative responses may occur during transplantation of the heart, lung, liver, kidney, and other body organs or organ systems.

Abnormal angiogenesis that may be treated using this invention include those abnormal angiogenesis accompanying rheumatoid arthritis, ischemic-reperfusion related brain edema and injury, cortical ischemia, ovarian hyperplasia and hypervascularity, polycystic ovary syndrome, endometriosis, psoriasis, diabetic retinopathy, and other ocular angiogenic diseases such as retinopathy of prematurity (retrolental fibroplastic), macular degeneration, corneal graft rejection, neuroscular glaucoma and Osler-Weber-Rendu syndrome.

Examples of diseases associated with uncontrolled angiogenesis that may be treated according to the present invention include, but are not limited to retinal/choroidal neovascularisation and corneal neovascularisation. Examples of diseases which include some component of retinal/choroidal neovascularisation include, but are not limited to, Best's diseases, myopia, optic pits, Stargart's diseases, Paget's disease, vein occlusion, artery occlusion, sickle cell anaemia, sarcoid, syphilis, pseudoxanthoma elasticum carotid apo structive diseases, chronic uveitis/vitritis, mycobacterial infections, Lyme's disease, systemic lupus erythematosus, retinopathy of prematurity, Eale's disease, diabetic retinopathy, macular degeneration, Bechet's diseases, infections causing a retinitis or chroiditis, presumed ocular histoplasmosis, pars planitis, chronic retinal detachment, hyperviscosity syndromes, toxoplasmosis, trauma and post-laser complications, diseases associated with rubesis (neovascularisation of the angle) and diseases caused by the abnormal proliferation of fibrovascular or fibrous tissue including all forms of proliferative vitreoretinopathy. Examples of corneal neovascularisation include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, diabetic retinopathy, retinopathy of prematurity, corneal graft rejection, Mooren ulcer, Terrien's marginal degeneration, marginal keratolysis, polyarteritis, Wegener sarcoidosis, Scleritis, periphigoid radial keratotomy, neovascular glaucoma and retrolental fibroplasia, syphilis, Mycobacteria infections, lipid degeneration, chemical burns, bacterial ulcers, fungal ulcers, Herpes simplex infections, Herpes zoster infections, protozoan infections and Kaposi sarcoma.

Chronic inflammatory diseases associated with uncontrolled angiogenesis may also be treated using PI3K inhibitors of the present invention. Chronic inflammation depends on continuous formation of capillary sprouts to maintain an influx of inflammatory cells. The influx and presence of the inflammatory cells produce granulomas and thus maintains the chronic inflammatory state. Inhibition of angiogenesis using a PI3K inhibitor alone or in conjunction with other anti-inflammatory agents may prevent the formation of the granulosmas and thus alleviate the disease. Examples of chronic inflammatory diseases include, but are not limited to, inflammatory bowel diseases such as Crohn's disease and ulcerative colitis, psoriasis, sarcoidosis, and rheumatoid arthritis.

Inflammatory bowel diseases such as Crohn's disease and ulcerative colitis are characterised by chronic inflammation and angiogenesis at various sites in the gastrointestinal tract. For example, Crohn's disease occurs as a chronic transmural inflammatory disease that most commonly affects the distal ileum and colon but may also occur in any part of the gastrointestinal tract from the mouth to the anus and perianal area. Patients with Crohn's disease generally have chronic diarrhoea associated with abdominal pain, fever, anorexia, weight loss and abdominal swelling. Ulcerative colitis is also a chronic, nonspecific, inflammatory and ulcerative disease arising in the colonic mucosa and is characterised by the presence of bloody diarrhoea. These inflammatory bowel diseases are generally caused by chronic granulomatous inflammation throughout the gastrointestinal tract, involving new capillary sprouts surrounded by a cylinder of inflammatory cells. Inhibition of angiogenesis by these inhibitors should inhibit the formation of the sprouts and prevent the formation of granulomas. Inflammatory bowel diseases also exhibit extra intestinal manifestations, such as skin lesions. Such lesions are characterized by inflammation and angiogenesis and can occur at many sites other the gastrointestinal tract. Inhibition of angiogenesis by PI3K inhibitors according to the present invention can reduce the influx of inflammatory cells and prevent lesion formation.

Sarcoidosis, another chronic inflammatory disease, is characterized as a multisystem granulomatous disorder. The granulomas of this disease can form anywhere in the body. Thus, the symptoms depend on the site of the granulomas and whether the disease is active. The granulomas are created by the angiogenic capillary sprouts providing a constant supply of inflammatory cells. By using PI3K inhibitors according to the present invention to inhibit angiogenesis, such granulomas formation can be inhibited. Psoriasis, also a chronic and recurrent inflammatory disease, is characterised by papules and plaques of various sizes. Treatment using these inhibitors alone or in conjunction with other anti-inflammatory agents should prevent the formation of new blood vessels necessary to maintain the characteristic lesions and provide the patient relief from the symptoms.

Rheumatoid arthritis (RA) is also a chronic inflammatory disease characterised by non-specific inflammation of the peripheral joints. It is believed that the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Treatment using PI3K inhibitors according to the present invention alone or in conjunction with other anti-RA agents may prevent the formation of new blood vessels necessary to maintain the chronic inflammation.

Preferably, the condition is cancer, notably leukaemias including chronic myelogenous leukaemia and acute myeloid leukaemia, lymphomas, solid tumours, and PTEN-negative tumours including PTEN-negative haematological, breast, lung, endometrial, skin, brain and prostate cancers (where PTEN refers to "phosphatise and tensin homolog deleted on chromosome 10"). More preferably, the condition to be treated in a patient in need thereof by administering an effective amount of a disclosed compound is a disorder selected from rheumatoid arthritis, asthma, chronic obstructive pulmonary disease (COPD), multiple sclerosis, psoriasis and other inflammatory skin disorders, systemic lupus erythematosus, inflammatory bowel disease, and organ transplant rejection. For example, provided herein is a method of treating a patient suffering a disorder selected from the group consisting leukaemias (including e.g., chronic myelogenous leukaemia and acute myeloid leukaemia), lymphoma, a solid tumour cancer such as breast, lung, or prostate cancer, PTEN-negative tumours including PTEN-negative haematological, breast, lung, endometrial, skin, brain and prostate cancers (where PTEN refers to "phosphatise and tensin homolog deleted on chromosome 10") comprising administering an effective amount of a disclosed compound.

The invention will now be illustrated by the following Examples.

EXAMPLES

Nomenclature: Compounds were named using Marvin-sketch 6.3.0 or higher

Analytical conditions: All $^1$H NMR were obtained at 300 or 400 MHz; all $^{19}$F NMR were obtained at 282 MHz.

| Abbreviations: | |
|---|---|
| rt room temperature | h hour |
| s singlet | d doublet |
| t triplet | q quartet |
| br broad | m multiplet |
| eq equivalent | min minute |
| ES$^+$ electrospray positive ionisation | MS mass spectrometry |
| ES$^-$ electrospray negative ionisation | |

Intermediates and Examples

Intermediate 1

Ethyl-3-amino-5-bromofuro[2,3-b]pyridine-2-carboxylate

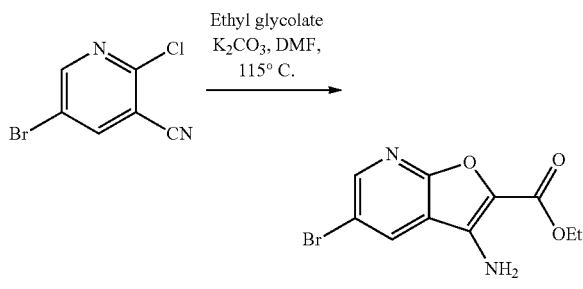

Intermediate 1

To a 10 L flask under N$_2$ (g) was added 5-bromo-2-chloropyridine-3-carbonitrile (435 g, 2.0 mol, 1 eq), DMF (2790 mL) and potassium carbonate (553 g, 4.0 mol, 2 eq). This was followed by the addition of ethyl glycolate (208.2 mL, 2.2 mol, 1.1 eq). The reaction mixture was heated to 115° C. overnight. Upon completion, the reaction mixture was cooled to rt and water (13.1 L) was added, this led to the formation of a precipitate. The mixture was stirred for 20 mins, then filtered. The resulting brown solid was dried at 50° C., slurried in Et$_2$O:heptane (9:1, 2.8 L) and filtered to give 405.6 g. Further purification via soxhlet extraction using TBME (4.5 L) yielded Intermediate 1 as a yellow solid (186 g, 34%).

¹H NMR (400 MHz, CDCl₃) $\delta_H$: 8.53 (d, J=2.0 Hz, 1H), 8.07 (d, J=2.0 Hz, 1H), 5.00 (br. s., 2H), 4.44 (q, J=7.0 Hz, 2H), 1.44 (t, J=7.0 Hz, 3H).

MS (ES⁺) 309 (100%, [M+Na]⁺), 307 (100%, [M+Na]⁺).

Intermediate 2

12-Bromo-8-oxa-3,5,10-triazatricyclo[7.4.0.0²,⁷]trideca-1(9),2(7),10,12-tetraene-4,6-dione

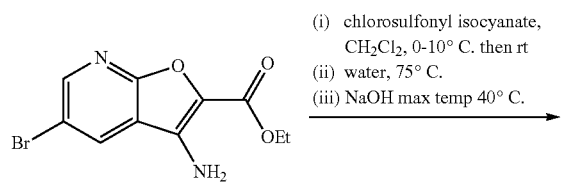

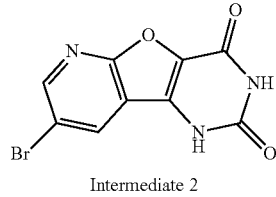

Intermediate 2

To Intermediate 1 (239.0 g, 0.84 mol, 1 eq) dissolved in CH₂Cl₂ (5.5 L) was added chlorosulfonyl isocyanate (87.6 mL, 1.0 mol, 1.2 eq) dropwise at 0-10° C. The resulting reaction mixture was stirred for 30 min, solvent removed by evaporation in vacuo and the resulting solid ground to a fine powder. Water (5.5 L) was added to the solid and the suspension was heated at 75° C. for 1 h. After cooling to rt, solid NaOH (335 g, 8.4 mol, 10 eq) was added, allowing the reaction to exotherm (maximum temperature 40° C.). The reaction was cooled to 0-10° C. and the pH adjusted to 5-6 using 5M HCl (~1 L). The reaction mixture was stirred for 30 mins, then filtered. The solid was washed with water (2.3 L) and pulled dry. Further drying in a vacuum oven at 40° C. yielded Intermediate 2 as a brown solid (193 g, 76%).

¹H NMR (400 MHz, DMSO-d₆) $\delta_H$: 12.01 (br s, 1H), 11.58 (br. s, 1H), 8.72 (d, J=2.0 Hz, 1H), 8.59 (d, J=2.0 Hz, 1H).

MS (ES⁻) 282 (100%, [M+H]⁺).

Intermediate 3

12-Bromo-4,6-dichloro-8-oxa-3,5,10-triazatricyclo[7.4.0.0²,⁷]trideca-1(9),2(7),3,5,10,12-hexaene

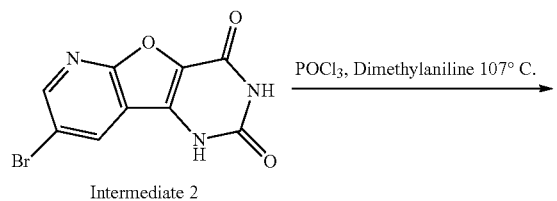

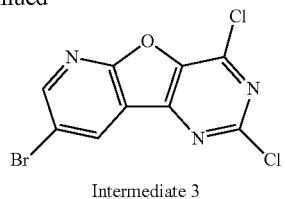

Intermediate 3

To Intermediate 2 (387 g, 1.27 mol, 1 eq) was added POCl₃ (6070 mL) and N,N-dimethylaniline (348 mL, 2.8 mol, 2.2 eq). The mixture was heated at 107° C. for 10 h. Once cooled to rt, solvent was removed in vacuo azeotroping with toluene (3×3.9 L). The resulting residue was partitioned between CH₂Cl₂ (12.76 L) and water (3.9 L) and the phases separated. The organic phase was washed with water (2×3.9 L). The combined aqueous was back-extracted with CH₂Cl₂ (7.7 L) and the combined organics dried over MgSO₄, filtered and stripped to yield Intermediate 3 as brown solid (429 g, ~quant.).

¹H NMR (400 MHz, CDCl₃) $\delta_H$: 8.78 (d, J=2.5 Hz, 1H), 8.72 (d, J=2.5 Hz, 1H).

Intermediate 4

12-Bromo-4-chloro-6-(morpholin-4-yl)-8-oxa-3,5,10-triazatricyclo[7.4.0.0²,⁷]trideca-1(9),2(7),3,5,10,12-hexaene

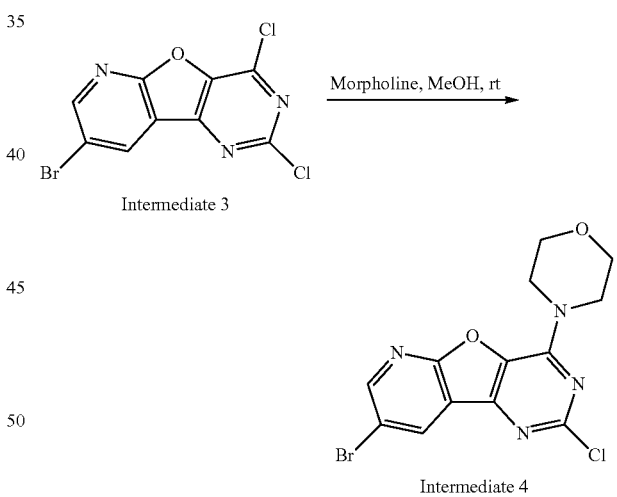

To Intermediate 3 (419.3 g, 1.32 mol, 1 eq) in MeOH (8588 mL) was added morpholine (259 mL, 2.90 mol, 2.2 eq) at rt. After stirring for 2 h, water (0.8 L) was added. The reaction mixture was cooled to 0-5° C. and stirred for an additional 30 mins. The resulting solid was filtered, washed with water (5.2 L) and pulled dry. Further purification by silica gel column chromatography with CH₂Cl₂/EtOAc (1:0-9:1) yielded Intermediate 4 (419 g, 84%).

¹H NMR (400 MHz, CDCl₃) $\delta_H$: 8.66 (d, J=2.0 Hz, 1H), 8.62 (d, J=2.0 Hz, 1H), 4.07-4.21 (m, 4H), 3.85-3.91 (m, 4H).

MS (ES⁺) 393 (100%, [M+Na]⁺), 391 (80%, [M+Na]⁺).

Intermediate 5

(2E)-3-[4-Chloro-6-(morpholin-4-yl)-8-oxa-3,5,10-triazatricyclo[7.4.0.0²,⁷]trideca-1(9),2(7),3,5,10,12-hexaen-12-yl]-N,N-dimethylprop-2-enamide

Intermediate 6

4-Chloro-6-(morpholin-4-yl)-8-oxa-3,5,10-triazatricyclo[7.4.0.0²,⁷]trideca-1(9),2(7),3,5,10,12-hexaene-12-carbaldehyde

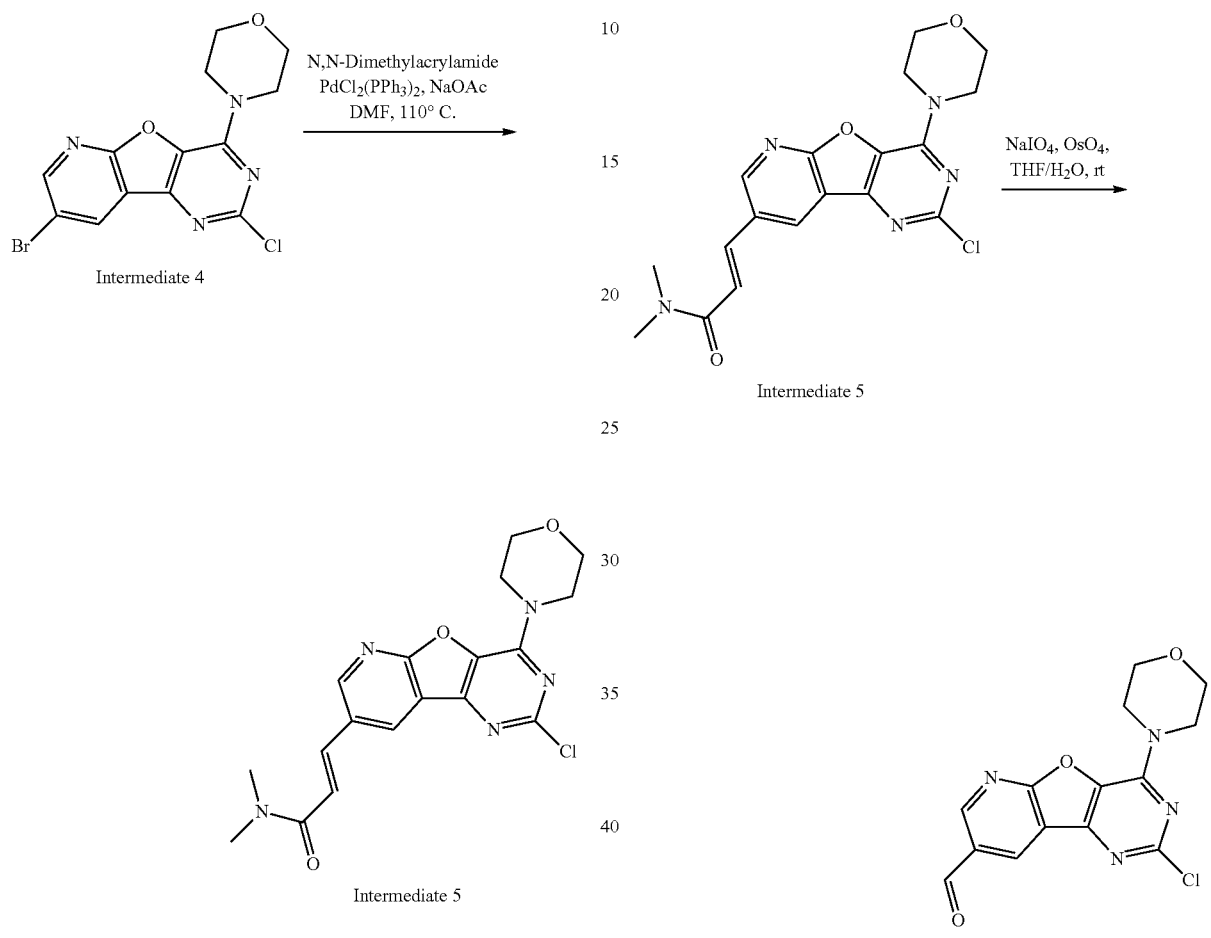

To Intermediate 4 (60 g, 0.15 mol, 1 eq) was added N,N-dimethylacrylamide (16.7 mL, 0.15 mol, 1 eq), PdCl$_2$(PPh$_3$)$_2$ (3.4 g, 4.5 mmol, 0.03 eq) and NaOAc (40 g, 0.45 mol, 3 eq) in DMF (1.2 L). The reaction mixture was heated at 110° C. for 7 h. This process was repeated 3 times and batches combined. Once cooled down to rt, the solvent was removed by evaporation in vacuo and the resulting residue was partitioned between CH$_2$Cl$_2$ (6.5 L) and water (5.5 L). The phases were separated and the aqueous phase was extracted with CH$_2$Cl$_2$ (2×4 L). The combined organics were washed with brine (2×4 L), dried over MgSO$_4$, filtered and the solvent removed by evaporation in vacuo. The resulting solid was slurried in EtOAc/heptane (1:1, 0.8 L) for 30 mins, filtered, washed and washed with EtOAc/heptane (1:1, 2×450 mL). Further drying in a vacuum oven at 40° C. yielded Intermediate 5 as an orange solid (203.0 g, 86%).

$^1$H NMR (400 MHz, CDCl$_3$) δ$_H$: 8.70 (s, 2H), 7.82 (d, J=15.6 Hz, 1H), 7.07 (d, J=15.6 Hz, 1H), 4.11-4.19 (m, 4H), 3.85-3.93 (m, 4H), 3.22 (s, 3H), 3.11 (s, 3H).

MS (ES$^+$) 388 (100%, [M+H]+).

Intermediate 5 (124.0 g, 0.39 mol, 1 eq) was dissolved in THF (12.4 L) at 65° C. Once cooled to 35° C., water (4.1 L), NaIO$_4$ (205.4 g, 1.17 mol, 3 eq) and OsO$_4$ (2.5 wt % in $^t$BuOH, 80.3 mL, 2%) were added. The reaction mixture was stirred at rt for 60 h. The reaction mixture was cooled to 0-5° C., stirred for 30 mins then filtered. The solid was washed with water (545 mL) and pulled dry. The crude product was combined with two further batches (2×118.3 g scale) and slurried in water (6.3 L) for 30 mins at rt. The solids were filtered, washed with water (1.6 L) and pulled dry. Further drying in a vacuum oven yielded Intermediate 6 as a pink solid (260 g, 88%)

$^1$H NMR (400 MHz, CDCl$_3$:MeOD, 9:1) δ$_H$: 10.13 (s, 1H), 9.04 (d, J=2.0 Hz, 1H), 8.91 (d, J=2.0 Hz, 1H), 3.99-4.13 (m, 4H), 3.73-3.84 (m, 4H).

MS (ES$^+$) 351 (100%, [M+MeOH+H]$^+$).

17

Intermediate 7

4-(6-Fluoro-1H-indol-4-yl)-6-(morpholin-4-yl)-8-oxa-3,5,10-triazatricyclo[7.4.0.0²,⁷]trideca-1(13),2(7),3,5,9,11-hexaene-12-carbaldehyde

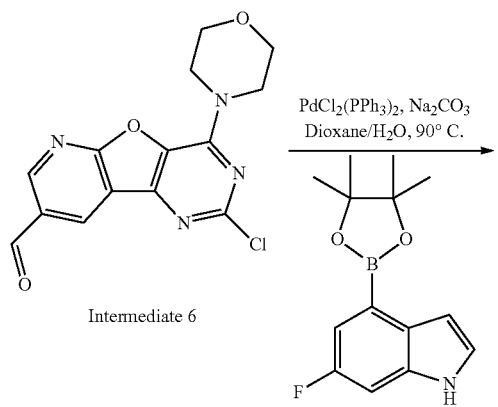

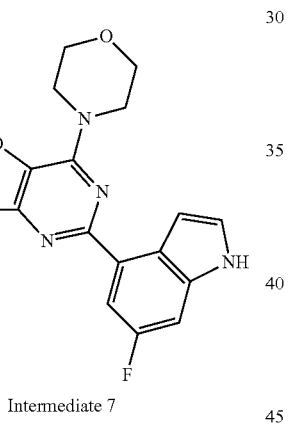

Intermediate 7

To Intermediate 6 (350 mg, 1.09 mmol, 1 eq) was added 6-fluoro-4-(tetramethyl-1,3,2-dioxaborolan-2-yl)-1H-indole (863 mg, 3.29 mmol, 3 eq), PdCl$_2$(PPh$_3$)$_2$ (153 mg, 0.22 mmol, 0.2 eq) and sodium carbonate (231 mg, 2.18 mmol, 2 eq) in dioxane (30 mL)/water (10 mL). Reaction mixture was heated at 90° C. for 3 h. It was then cooled to 60-70° C. Water (20 mL) and EtOAc (50 mL) were added. The phases were separated and the aqueous phase extracted with EtOAc (3×50 mL) at 60-65° C. The combined organics were dried over MgSO$_4$, filtered and the solvent was removed by evaporation in vacuo. After purification by silica gel column chromatography with CH$_2$Cl$_2$/MeOH (1:0-4:1), the resulting solid was triturated in CH$_2$Cl$_2$ (5 mL), filtered and washed with CH$_2$Cl$_2$ (2×2 mL). Following drying, Intermediate 7 was obtained as a yellow brown solid (50 mg, 15%).

$^1$H NMR (300 MHz, DMSO-d$_6$) $\delta_H$: 11.35 (br s, 1H), 10.23 (s, 1H), 9.10 (dd, J=19.2, 2.1 Hz, 2H), 7.91 (dd, J=11.5, 2.4 Hz, 1H), 7.45-7.55 (m, 2H), 7.32 (dd, J=9.2, 1.7 Hz, 1H), 4.02-4.14 (m, 4H), 3.80-3.90 (m, 4H).

MS (ES$^+$) 449.8 (100%, [M+MeOH+H]$^+$).

18

Intermediate 8

4-(5-Fluoro-1H-indol-4-yl)-6-(morpholin-4-yl)-8-oxa-3,5,10-triazatricyclo[7.4.0.0²,⁷]trideca-1(13),2(7),3,5,9,11-hexaene-12-carbaldehyde

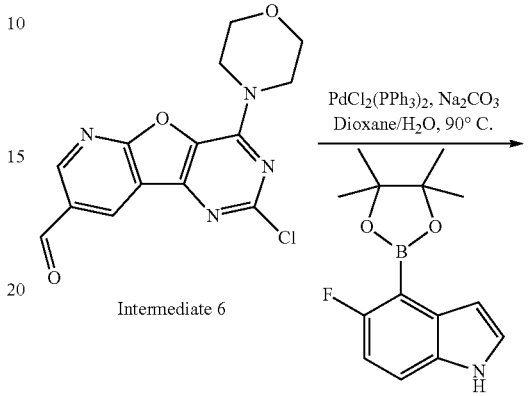

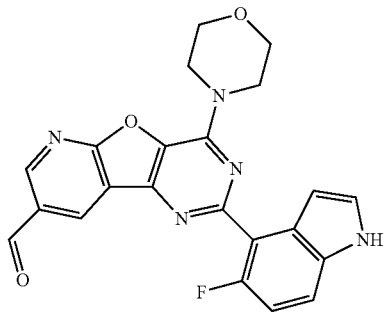

Intermediate 8

To Intermediate 6 (353 mg, 1.10 mmol, 1 eq) was added 5-fluoro-4-(tetramethyl-1,3,2-dioxaborolan-2-yl)-1H-indole (870 mg, 3.32 mmol, 3 eq), PdCl$_2$(PPh$_3$)$_2$ (155 mg, 0.22 mmol, 0.2 eq) and sodium carbonate (233 mg, 2.2 mmol, 2 eq) in dioxane (30 mL)/water (10 mL). Reaction mixture was heated at 90° C. for 2 h. It was then cooled to 60-70° C. Water (20 mL) and EtOAc (50 mL) were added. The phases were separated and the aqueous phase extracted with EtOAc (3×50 mL) at 60-65° C. The combined organics were dried over MgSO$_4$, filtered and the solvent was removed by evaporation in vacuo. The resulting solid was triturated in CH$_2$Cl$_2$ (5 mL), filtered and washed with CH$_2$Cl$_2$ (2×2 mL). Following drying, Intermediate 8 was obtained as a grey solid (275 mg, 60% yield).

$^1$H NMR (300 MHz, DMSO-d$_6$) $\delta_H$: 11.32 (br s, 1H), 10.27 (s, 1H), 9.19 (d, J=2.1 Hz, 1H), 9.08 (d, J=2.1 Hz, 1H), 7.41-7.56 (m, 2H), 7.04 (dd, J=11.2, 8.8 Hz, 1H), 6.79 (d, J=2.1 Hz, 1H), 3.99-4.16 (m, 4H), 3.75-3.90 (m, 4H).

MS (ES$^+$) 449.8 (100%, [M+MeOH+H]$^+$).

Intermediate 9

6-(Morpholin-4-yl)-4-[2-(trifluoromethyl)-1H-indol-4-yl]-8-oxa-3,5,10-triazatricyclo[7.4.0.0²,⁷]trideca-1(13),2(7),3,5,9,11-hexaene-12-carbaldehyde

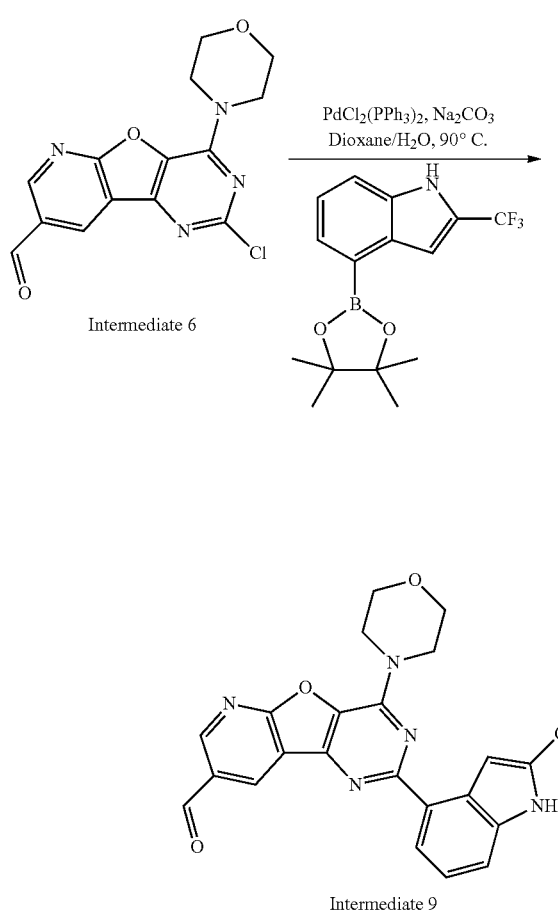

To Intermediate 6 (340 mg, 1.07 mmol, 1 eq) was added 4-(tetramethyl-1,3,2-dioxaborolan-2-yl)-2-(trifluoromethyl)-1H-indole (1.0 g, 3.20 mmol, 3 eq), PdCl₂(PPh₃)₂ (150 mg, 0.21 mmol, 0.2 eq) and sodium carbonate (227 mg, 2.1 mmol, 2 eq) in dioxane (30 mL)/water (10 mL). Reaction mixture was heated at 90° C. overnight. It was then cooled to 60-70° C. Water (20 mL) and EtOAc (50 mL) were added. The phases were separated and the aqueous phase extracted with EtOAc (3×50 mL) at 60-65° C. The combined organics were dried over MgSO₄, filtered and the solvent was removed by evaporation in vacuo. The resulting solid was triturated in CH₂Cl₂ (5 mL), filtered and washed with CH₂Cl₂ (2×2 mL). Following drying, Intermediate 9 was obtained as a grey solid (252 mg, 50% yield).

¹H NMR (300 MHz, DMSO-d₆) δ$_H$: 12.46 (s, 1H), 10.26 (s, 1H), 9.15 (d, J=2.1 Hz, 1H), 9.04 (d, J=2.1 Hz, 1H), 8.26 (dd, J=7.3, 0.8 Hz, 1H), 7.99 (s, 1H), 7.63 (d, J=8.3 Hz, 1H), 7.39-7.48 (m, 1H), 4.10 (m, 4H), 3.86 (m, 4H).

MS (ES⁺) 467.8 (100%, [M+H]⁺).

Intermediate 10

4-Chloro-12-[(3-methoxyazetidin-1-yl)methyl]-6-(morpholin-4-yl)-8-oxa-3,5,10-triazatricyclo[7.4.0.0²,⁷]trideca-1(13),2(7),3,5,9,11-hexaene

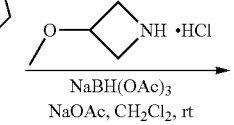

To a suspension of Intermediate 6 (2.0 g, 6.28 mmol, 1 eq), 3-methoxyazetidine hydrochloride (1.94 g, 15.7 mmol, 2.5 eq) and NaOAc (1.29 g, 15.7 mmol, 2.5 eq) in anhydrous 1,2-dichloroethane (80 mL) was added NaBH(OAc)₃ (2.66 g, 12.6 mmol, 2 eq). The reaction mixture was stirred at rt for 1 h. Then, it was partitioned with 0.5N NaOH (50 mL) and extracted with CH₂Cl₂ (2×30 mL). The combined organic extracts were dried over MgSO₄, filtered and the solvent was removed by evaporation in vacuo. Purification by silica gel column chromatography with EtOAc/MeOH (1:0-19:1) followed by recrystallization from EtOAc yielded Intermediate 10 as an off-white solid (1.61 g, 66%).

¹H NMR (300 MHz, DMSO-d₆) δ$_H$: 8.56 (d, J=2.3 Hz, 1H), 8.43 (d, J=2.3 Hz, 1H), 3.92-4.08 (m, 5H), 3.72-3.86 (m, 6H), 3.46-3.54 (m, 2H), 3.15 (s, 3H), 2.89-2.99 (m, 2H).

MS (ES⁺) 390.1 (100%, [M+H]⁺).

Intermediate 11

Ethyl 3-amino-5-bromothieno[2,3-b]pyridine-2-carboxylate

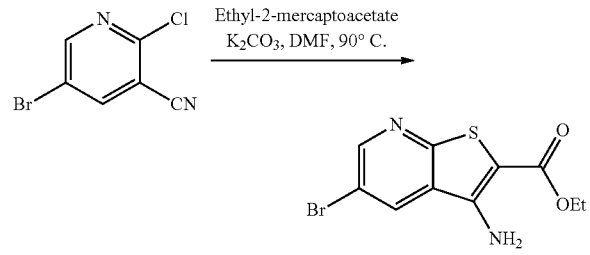

To a suspension of 5-bromo-2-chloropyridine-3-carbonitrile (5 g, 0.023 mol, 1 eq) in ethanol (15 mL) under argon atmosphere, was added Na$_2$CO$_3$ (5.12 g, 0.048 mol, 2 eq) and ethyl-2-mercaptoacetate (3.56 g, 0.029 mol, 1.26 eq) and the reaction mixture was heated at 90° C. for 7 h. Then the reaction mixture was cooled and filtered. The filtrate was kept aside and the residue obtained was washed with 20% MeOH in CH$_2$Cl$_2$ and filtered. The filtrate was concentrated in vacuo to afford 5.5 g (80%) of Intermediate 11.

$^1$H NMR (400 MHz, CDCl$_3$) $\delta_H$: 8.70 (br s, 1H), 8.06 (br s, 1H), 5.85 (br s, 2H), 4.38 (q, 2H), 1.39 (t, J=7.2 Hz, 3H). MS (ES$^+$)=302 (100%, [M+H]$^+$)

Intermediate 12

12-Bromo-8-thia-3,5,10-triazatricyclo[7.4.0.0$^{2,7}$] trideca-1(9),2(7),10,12-tetraene-4,6-dione

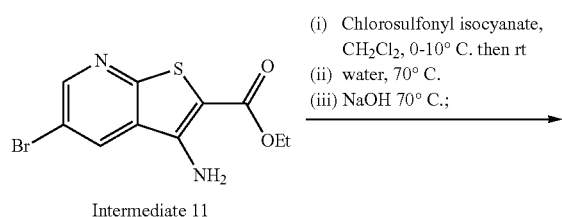

To a solution of Intermediate 11 (10 g, 0.03 3 mol, 1 eq) in CH$_2$Cl$_2$ (300 mL) under an argon atmosphere at 0° C. was added chlorosulfonylisocyanate (3.8 mL, 0.043 mol, 1.3 eq). The reaction mixture was allowed to warm to room temperature (over 2 h) and then concentrated in vacuo. To this mixture water (160 mL) was added and heated at 70° C. for 4 h. Then the reaction mixture was cooled to rt and NaOH (13 g, 0.32 mol, 20 eq) was added and reaction mixture was heated at 70° C. for 2 h. After completion of the reaction, the pH of the reaction mixture was adjusted to 6 using 1M HCl. The solid obtained were filtered through a Buchner funnel and washed with water (300 mL) and MeOH (300 mL), dried well under reduced pressure to yield 4.4 g (45%) of Intermediate 12.

$^1$H NMR (400 MHz, CDCl$_3$) $\delta_H$: 8.97 (s, 1H) 8.90 (s, 1H).

Intermediate 13

12-bromo-4,6-dichloro-8-thia-3,5,10-triazatricyclo [7.4.0.0$^2$]trideca-1(9),2(7),3,5,10,12-hexaene To Intermediate 12 (10 g, 0.033 mol, 1 eq), POCl$_3$ (156 mL, 1.67 mol, 50 eq) was added portion wise under argon at 0° C. over 10-15 min. To the reaction mixture N,N-dimethylaniline (8.46 mL, 0.067 mol, 2 eq) was added drop wise at 0° C. under argon atmosphere and reaction mixture was heated at 120° C. for 5 h, (the reaction was monitored by TLC). The reaction mixture was then cooled to rt and POCl$_3$ was evaporated under vacuum, the residue was stripped with ethylene dichloride. Water was added to reaction mixture and the mixture was extracted multiple times with ethyl acetate. The combined organic layers was dried over Na$_2$SO$_4$, filtered and the solvent removed by evaporation in vacuo to afford 7 g (62.3%) of Intermediate 13.

$^1$H NMR (400 MHz, CDCl$_3$) $\delta_H$: 8.93 (br s, 1H) 8.8 (br s, 1H).

Intermediate 14

12-Bromo-4-chloro-6-(morpholin-4-yl)-8-thia-3,5, 10-triazatricyclo[7.4.0.0$^{2,7}$]trideca-1(9),2(7),3,5,10, 12-hexaene To a suspension of Intermediate 13 (8 g, 0.018 mol, 1 eq) in methanol (150 mL) and dichloromethane (150 mL) was added morpholine (5.2 mL, 0.056 mol, 2.4 eq). The reaction mixture was stirred at rt for 4 h (monitored by TLC). After completion of the reaction, dichloromethane was removed by evaporation in vacuo and the residue in methanol was diluted with ice-water and stirred for 30 min. The solid obtained was filtered, washed with water (100 mL) and dried to yield 7 g (76%) of Intermediate 14.

$^1$H NMR (400 MHz, CDCl$_3$) $\delta_H$: 8.82 (br s, 2H), 4.04 (m, 4H), 3.89 (m, 4H).

MS (ES$^+$)=387 (100%, [M+H]$^+$).

Intermediate 15

(2E)-3-[4-Chloro-6-(morpholin-4-yl)-8-thia-3,5,10-triazatricyclo[7.4.0.0$^{2,7}$]trideca-1(9),2(7),3,5,10,12-hexaen-12-yl]-N,N-dimethylprop-2-enamide

Intermediate 16

4-Chloro-6-(morpholin-4-yl)-8-thia-3,5,10-triazatricyclo[7.4.0.0$^{2,7}$]trideca-1(9),2(7),3,5,10,12-hexaene-12-carbaldehyde

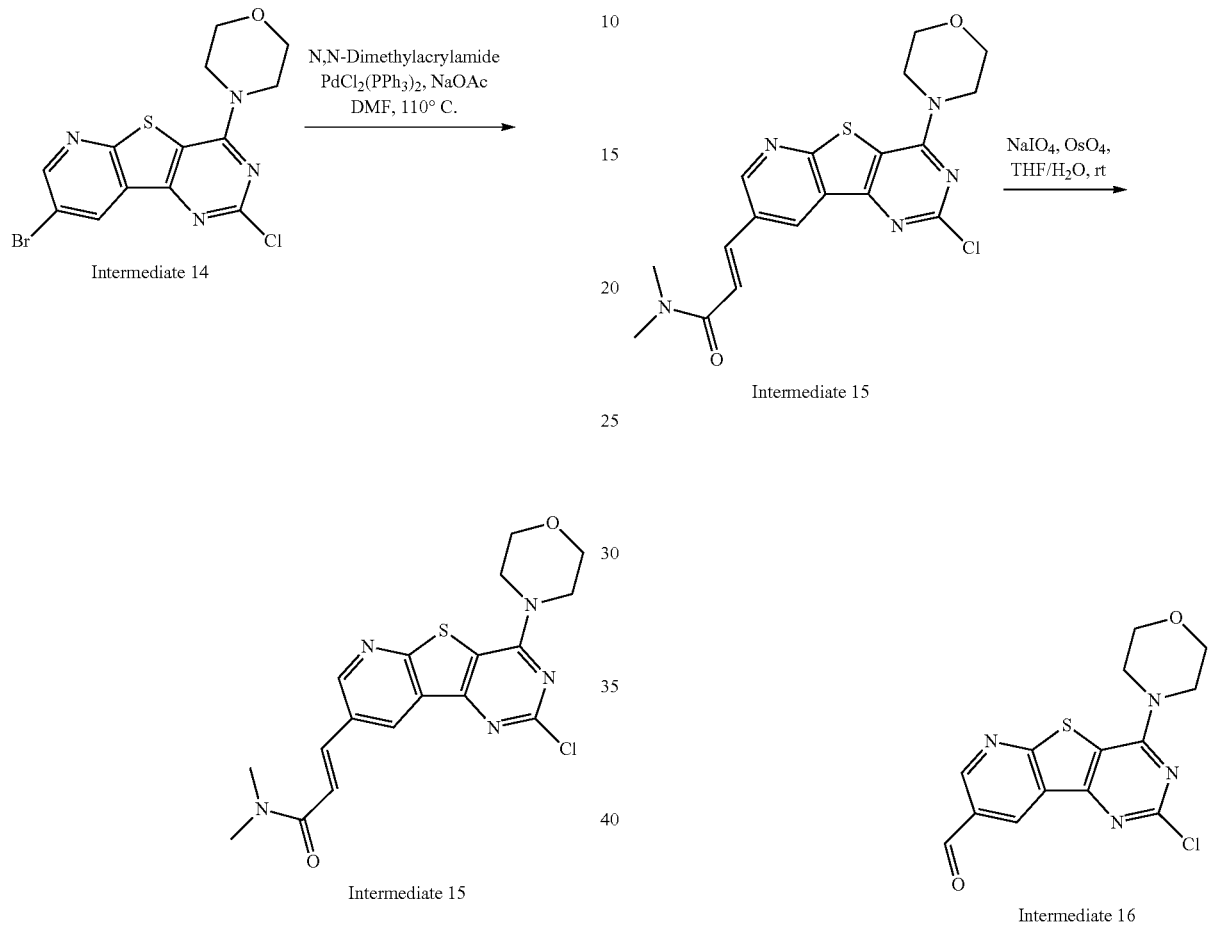

Intermediate 14 (5 g, 0.0129 mol, 1 eq) was dissolved in DMF (50 mL) and N, N-dimethylacrylamide (1.3 mL, 0.0129 mol, 1 eq) and sodium acetate (3.1 g, 0.038 mol, 3 eq) was added and the reaction mixture was degassed for 30 min using argon. Then Pd(PPh$_3$)$_2$Cl$_2$ (0.275 g, 0.0004 mol, 0.03 eq) was added and the reaction mixture was again degassed with argon for 15 min. The reaction mixture was heated at 110° C. for 5 h, (the reaction was monitored by TLC and LCMS). After completion of reaction, the reaction mixture was cooled to rt and then diluted with CH$_2$Cl$_2$ (500 mL) and washed with ice-cold water (2×125 mL). The combined organic layers was dried over Na$_2$SO$_4$ and then the solvent removed by evaporation in vacuo to yield a solid residue. The residue was triturated with ethyl acetate (50 mL) and filtered to yield 4.5 g (86%) of Intermediate 15.

$^1$H NMR (400 MHz, CDCl$_3$) $\delta_H$: 8.86 (br s, 2H), 7.82 (d, J=15.2 Hz, 1H), 7.17 (d, J=15.2 Hz, 1H), 4.06 (m, 4H), 3.90 (m, 4H), 3.24 (s, 3H), 3.11 (s, 3H).

MS (ES$^+$)=404 (100%, [M+H]$^+$).

Intermediate 15 (5 g, 0.0123 mol, 1 eq) was taken up in THF: water (75 mL: 75 mL) and heated to 70° C. to dissolve the compound. To the reaction mixture were added sodium metaperiodate (8 g, 0.37 mol, 3 eq) followed by OsO$_4$ (2% solution in t-BuOH, 26 mL, 0.002 mol, 0.17 eq) and the reaction mixture was stirred at rt for 18 h. The reaction mixture was quenched with sat. sodium thiosulfate solution. THF and t-BuOH were removed by evaporation in vacuo to give a suspension of the product in water. The mixture was cooled to rt and the solid was isolated by filtration, the residue was stirred in deionised water and filtered. The solid was dried under high vacuum to yield 3.3 g (67%) of Intermediate 16.

$^1$H NMR (400 MHz, DMSO-d$_5$) $\delta_H$: 10.26 (s, 1H), 9.25 (br s, 1H), 9.15 (br s, 1H), 3.96 (m, 4H), 3.82 (m, 4H).

$^1$H NMR (400 MHz, CDCl$_3$) $\delta_H$: 10.26 (s, 1H), 9.25 (br s, 1H), 9.15 (br s, 1H), 4.12 (m, 4H), 3.89 (m, 4H).

MS (ES$^+$)=335 (100%, [M+H]$^+$).

Intermediate 17

4-Chloro-12-[(3-methoxyazetidin-1-yl)methyl]-6-(morpholin-4-yl)-8-thia-3,5,10-triazatricyclo[7.4.0.0²,⁷]trideca-1(13),2(7),3,5,9,11-hexaene

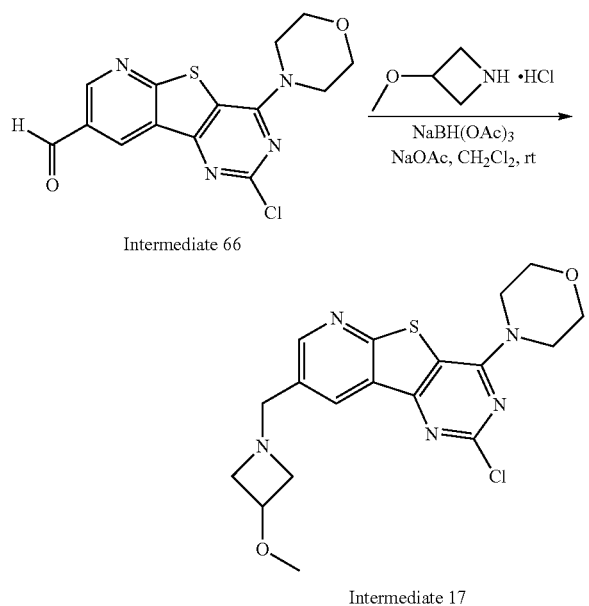

Intermediate 17

To a suspension of Intermediate 16 (3.02 g, 8.96 mmol, 1 eq), 3-methoxyazetidine hydrochloride (2.22 g, 18.0 mmol, 2 eq) and NaOAc (1.48 g, 18 mmol, 2 eq) in anhydrous CH$_2$Cl$_2$ (50 mL) was added NaBH(OAc)$_3$ (3.81 g, 18.0 mmol, 2 eq). The reaction mixture was stirred at rt overnight. Then, it was partitioned with 1N NaOH (100 mL) and extracted with CH$_2$Cl$_2$ (2×100 mL). The combined organic extracts were dried over MgSO$_4$, filtered and the solvent was removed in vacuo. Purification by silica gel column chromatography with CH$_2$Cl$_2$/MeOH (1:0-24:1), then EtOAc/MeOH (1:0-19:1) yielded Intermediate 17 as a white solid (1.87 g, 54%).

$^1$H NMR (300 MHz, DMSO-d$_6$) $\delta_H$: 8.78 (d, J=2.1 Hz, 1H), 8.50 (d, J=2.1 Hz, 1H), 3.98-4.06 (m, 1H), 3.90-3.97 (m, 4H), 3.82 (s, 2H), 3.74-3.80 (m, 4H), 3.48-3.57 (m, 2H), 3.15 (s, 3H), 2.91-3.00 (m, 2H).

MS (ES$^+$) 406.1 (100%, [M+H]$^+$).

Intermediate 18

7-Fluoro-4-(4,4,5,5-tetramethyl-1,3,2-dioxaborolan-2-yl)-1H-indole

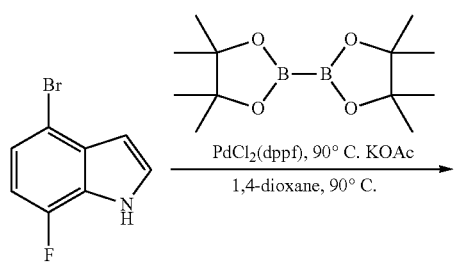

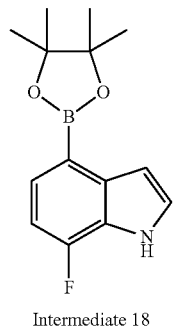

Intermediate 18

A solution of 4-bromo-7-fluoroindole (863 mg, 4.03 mmol, 1.0 eq) in 1,4-dioxane (10 mL) was degassed with argon for 5 min before the addition of bis(pinacolato)diboron (1.33 g, 5.24 mmol, 1.3 eq). Whilst degassing, potassium acetate (1.19 g, 12.1 mmol, 3.0 eq) and PdCl$_2$(dppf) (88.5 mg, 0.121 mmol, 3 mol %) were added. The vessel was then sealed and stirred at 90° C. for 2 h. Upon cooling, the reaction mixture was poured into 50% brine (50 mL) and extracted with EtOAc (3×30 mL). The combined organic extracts were dried over MgSO$_4$, filtered and concentrated in vacuo. Purification by silica gel column chromatography with hexane/CH$_2$Cl$_2$ (1:0-3:2) yielded Intermediate 18 as a cream solid (691 mg, 66%).

$^1$H NMR (300 MHz, CDCl$_3$) $\delta_H$: 8.35 (br s, 1H), 7.58 (dd, J=7.8, 5.4 Hz, 1H), 7.28-7.31 (m, 1H), 7.08 (td, J=3.4, 2.3 Hz, 1H), 6.92 (dd, J=11.2, 7.8 Hz, 1H), 1.39 (s, 12H).

$^{19}$F NMR (282 MHz, CDCl$_3$) $\delta_F$: −131.02—130.92 (m, 1F).

MS (ES$^+$) 262.1 (100%, [M+H]$^+$), 284.0 (25%, [M+Na]$^+$).

Intermediate 19

4-Chloro-6,12-bis(morpholin-4-yl)-8-oxa-3,5,10-triazatricyclo[7.4.0.0²,⁷]trideca-1(9),2,4,6,10,12-hexaene

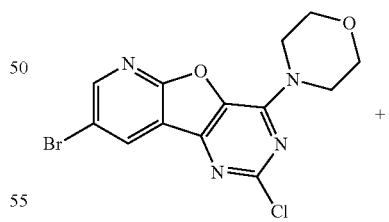

Intermediate 4

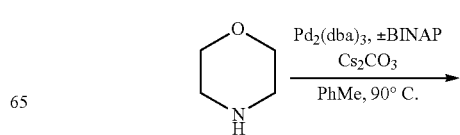

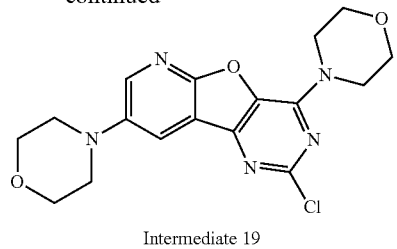

Intermediate 19

To a flask containing Intermediate 4 (500 mg, 1.35 mmol, 1.0 eq), cesium carbonate (661 mg, 2.03 mmol, 1.5 eq), Pd$_2$(dba)$_3$ (63.8 mg, 0.0676 mmol, 5 mol %) and ±BINAP (84.1 mg, 0.135 mmol, 10 mol %) was added toluene (35 mL) and morpholine (142 µL, 1.62 mmol, 1.2 eq). The reaction mixture was stirred at 90° C. for 16 h. After cooling to rt, additional portions of cesium carbonate (220 mg, 0.676 mmol, 0.5 eq), Pd$_2$(dba)$_3$ (63.8 mg, 0.0676 mmol, 5 mol %) and ±BINAP (84.1 mg, 0.135 mmol, 10 mol %) were added and the reaction mixture was stirred at 90° C. for a further 2 h. The mixture was cooled to rt, poured into H$_2$O (50 mL) and extracted with EtOAc (3×20 mL). The combined organic extracts were dried over MgSO$_4$, filtered and concentrated in vacuo. A separate, additional reaction was carried out using Intermediate 4 (77.0 mg, 0.208 mmol, 1.0 eq), employing an identical procedure and stirring at 90° C. for 16 h, without recharging with additional reagents. The crude residues were combined for purification three times by silica gel chromatography using CH$_2$Cl$_2$/MeOH (1:0-49:1) then hexane/EtOAc (1:0-2:3) then CH$_2$Cl$_2$/EtOAc (1:0-3:2), yielding Intermediate 19 as a pale yellow solid (313 mg, 53%).

$^1$H NMR (300 MHz, DMSO-d$_6$) δ$_H$: 8.46 (d, J=3.0 Hz, 1H), 8.00 (d, J=2.8 Hz, 1H), 3.90-4.08 (m, 4H), 3.68-3.85 (m, 8H), 3.17-3.28 (m, 4H).

MS (ES$^+$) 376.1 (80%, [M+H]$^+$).

Intermediate 20

4-{[12-chloro-10-(morpholin-4-yl)-8-oxa-6-azatricyclo[7.4.0.0$^{2,7}$]trideca-1(13),2,4,6,9,11-hexaen-4-yl]methyl}-1-ethylpiperazin-2-one

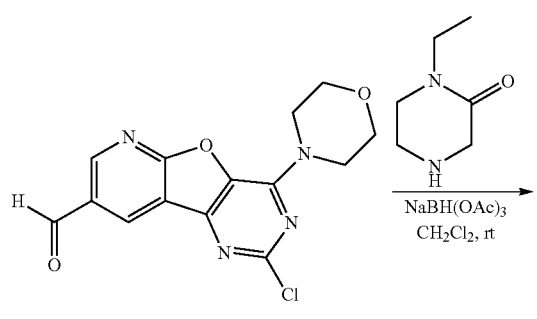

Intermediate 6

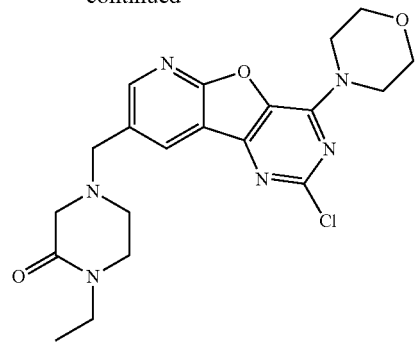

Intermediate 20

To a solution of 1-ethylpiperazin-2-one (2.60 g, 19.3 mmol, 3.0 eq) in anhydrous CH$_2$Cl$_2$ (200 mL) was added Intermediate 6 (2.05 g, 6.42 mmol, 1.0 eq) followed by NaBH(OAc)$_3$ (2.72 g, 12.8 mmol, 2.0 eq). The reaction mixture was stirred at rt for 16 h then poured into H$_2$O (200 mL) and extracted with CH$_2$Cl$_2$ (2×100 mL). The combined organic extracts were dried over MgSO$_4$, filtered, and concentrated in vacuo. Purification by silica gel chromatography with EtOAc/MeOH (1:0-16:1) yielded Intermediate 20 as a white solid (2.64 g, 95%).

$^1$H NMR (300 MHz, DMSO-d$_6$) δ$_H$: 8.55 (d, J=2.3 Hz, 1H), 8.51 (d, J=2.1 Hz, 1H), 4.09-4.19 (m, 4H), 3.79-3.93 (m, 4H), 3.71-3.77 (m, 2H), 3.45 (q, J=7.2 Hz, 2H), 3.34 (t, J=5.4 Hz, 2H), 3.18 (s, 2H), 2.74 (t, J=5.5 Hz, 2H), 1.16 (t, J=7.2 Hz, 3H).

MS (ES$^+$) 431.0 (100%, [M+H]$^+$), 453.0 (10%, [M+Na]$^+$).

Intermediate 21

3-fluoro-4-(4,4,5,5-tetramethyl-1,3,2-dioxaborolan-2-yl)-1H-indole

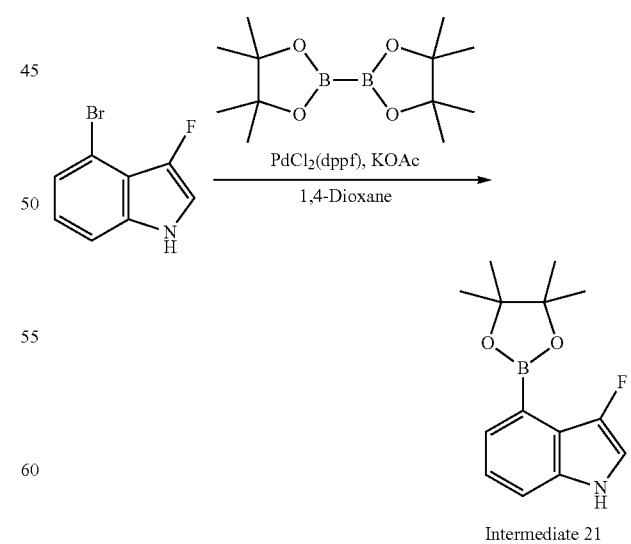

Intermediate 21

To a mixture of 4-bromo-3-fluoro-1H-indole (950 mg, 4.45 mmol, 1 eq), bis(pinacolato)diboron (1.24 g, 4.9 mmol, 1.1 eq), potassium acetate (1.31 g, 13.3 mmol, 3 eq) and PdCl$_2$(dppf) (162 mg, 0.22 mmol, 0.05 eq) was added dioxane (29 mL). The resultant suspension was degassed with Ar(g) and heated to 85° C. for 20 h. The reaction mixture was partitioned between EtOAc (200 mL), water (100 mL) and brine (100 mL). The aqueous phase was re-extracted with EtOAc (2×50 mL) and the combined organics were washed with brine (50 mL), dried over MgSO4, filtered and concentrated in vacuo. Purification by silica gel column chromatography with hexane/CH$_2$Cl$_2$ (1:0-5:7) yielded Intermediate 21 as a light green solid (458 mg, 39%).

$^1$H NMR (DMSO-d$_5$) δ$_H$: 10.65-11.10 (m, 1H), 7.46 (ddd, J=8.1, 2.7, 1.0 Hz, 1H), 7.37 (dd, J=7.0, 0.9 Hz, 1H), 7.32 (t, J=2.6 Hz, 1H), 7.12 (dd, J=8.2, 7.1 Hz, 1H), 1.21-1.40 (m, 12H).

Example A 4-(6-Fluoro-1H-indol-4-yl)-6-(morpholin-4-yl)-12-[(1S,4S)-2-oxa-5-azabicyclo[2.2.1]heptan-5-ylmethyl]-8-oxa-3,5,10-triazatricyclo[7.4.0.0$^{2,7}$]trideca-1(13),2(7),3,5,9,11-hexaene and the solvent was removed by evaporation in vacuo. The residue was dissolved in CH$_2$Cl$_2$/MeOH (1:1, 20 mL) and swirled with MP-TMT resin (150 mg, 5 eq) overnight. The resin was then filtered off, washed with CH$_2$Cl$_2$/MeOH (1:1, 20 mL) and the solvent was removed in vacuo. Purification by silica gel column chromatography with EtOAc/MeOH (1:0-6:1) yielded Example A as a white solid (18.1 mg, 60%).

$^1$H NMR (300 MHz, CDCl$_3$) δ$_H$: 8.64 (d, J=1.9 Hz, 1H), 8.59 (d, J=1.9 Hz, 1H), 8.33 (br s, 1H), 8.02 (dd, J=11.3, 2.3 Hz, 1H), 7.58-7.66 (m, 1H), 7.37 (t, J=2.6 Hz, 1H), 7.22 (dd, J=8.5, 1.7 Hz, 1H), 4.43-4.51 (m, 1H), 4.22-4.31 (m, 4H), 4.19 (d, J=7.9 Hz, 1H), 3.90-4.03 (m, 6H), 3.70 (dd, J=7.6, 1.2 Hz, 1H), 3.54 (s, 1H), 2.94 (d, J=9.8 Hz, 1H), 2.64 (d, J=10.2 Hz, 1H), 1.97 (d, J=8.7 Hz, 1H), 1.80 (d, J=9.2 Hz, 1H).

MS (ES$^+$) 500.9 (100%, [M+H]$^+$).

Example B 4-(6-Fluoro-1H-indol-4-yl)-6-(morpholin-4-yl)-12-{2-oxa-7-azaspiro[3.5]nonan-7-ylmethyl}-8-oxa-3,5,10-triazatricyclo[7.4.0.0$^{2,7}$]trideca-1(13),2(7),3,5,9,11-hexaene

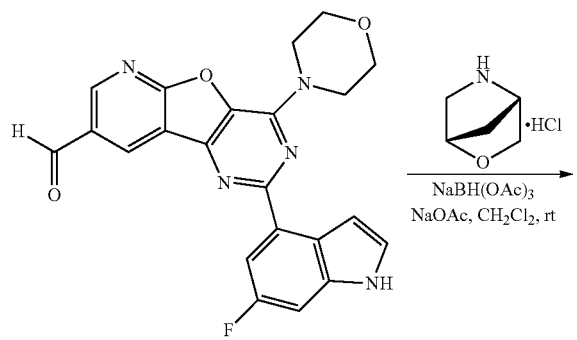

Intermediate 7

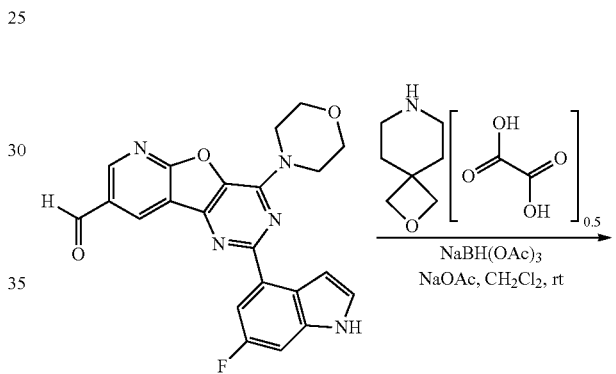

Intermediate 7

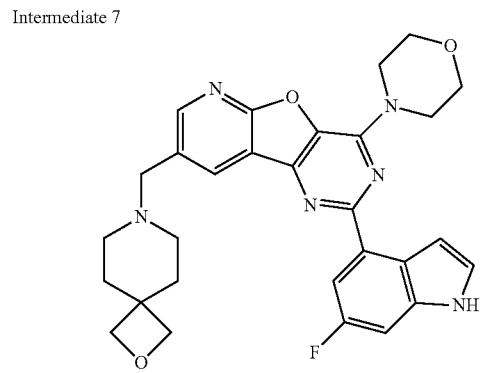

Example A

Example B

To a suspension of Intermediate 7 (25 mg, 0.06 mmol, 1 eq), (1S,4S)-2-oxa-5-azabicyclo[2.2.1]heptane hydrochloride (25 mg, 0.18 mmol, 3 eq) and NaOAc (15 mg, 0.18 mmol, 3 eq) in anhydrous CH$_2$Cl$_2$ (5 mL) was added NaBH(OAc)$_3$ (26 mg, 0.12 mmol, 2 eq). The reaction mixture was stirred at rt overnight. It had not reached completion, thus more reagents were added: (1S,4S)-2-oxa-5-azabicyclo[2.2.1]heptane hydrochloride (9 mg, 0.06 mmol, 1 eq) and NaOAc (5 mg, 0.06 mmol, 1 eq). The mixture was left to stir at rt overnight. Then, it was partitioned with H$_2$O (10 mL) and extracted with CH$_2$Cl$_2$ (3×10 mL). The combined organic extracts were dried over MgSO$_4$ To a suspension of Intermediate 7 (25 mg, 0.06 mmol, 1 eq), 2-oxa-7-azaspiro[3.5]nonane hemioxalate (31 mg, 0.18 mmol, 3 eq) and NaOAc (15 mg, 0.18 mmol, 3 eq) in anhydrous CH$_2$Cl$_2$ (5 mL) was added NaBH(OAc)$_3$ (25 mg, 0.12 mmol, 2 eq). The reaction mixture was stirred at rt over 4 days. Each day, more reagents were added: 2-oxa-7-azaspiro[3.5]nonane hemioxalate (10 mg, 0.06 mmol, 1 eq) and NaOAc (5 mg, 0.06 mmol, 1 eq), as the reaction had not reached completion. The reaction mixture was partitioned with H$_2$O (10 mL) and extracted with CH$_2$Cl$_2$ (3×10 mL). The combined organic extracts were dried over MgSO$_4$ and the solvent was removed by evaporation in vacuo. The residue was dissolved in CH$_2$Cl$_2$/MeOH (1:1, 20 mL) and swirled with MP-TMT resin (150 mg, 5 eq) overnight. The resin was then filtered off, washed with CH$_2$Cl$_2$/MeOH (1:1, 20 mL) and the solvent was removed by evaporation in vacuo. Purification by silica gel column chromatography with EtOAc/MeOH (1:0-6:1) yielded Example B as a white solid (22.3 mg, 70%).

$^1$H NMR (300 MHz, CDCl$_3$) δ$_H$: 8.58 (d, J=2.1 Hz, 1H), 8.53 (d, J=2.1 Hz, 1H), 8.34 (br s, 1H), 8.02 (dd, J=11.2, 2.4 Hz, 1H), 7.61 (t, J=2.3 Hz, 1H), 7.32-7.40 (m, 1H), 7.22 (dd, J=8.8, 2.2 Hz, 1H), 4.43 (s, 4H), 4.21-4.30 (m, 4H), 3.90-3.99 (m, 4H), 3.67 (s, 2H), 2.27-2.51 (m, 4H), 1.86-1.96 (m, 4H).

MS (ES$^+$) 528.8 (100%, [M+H]$^+$).

Example C 4-(5-Fluoro-1H-indol-4-yl)-6-(morpholin-4-yl)-12-[(1S,4S)-2-oxa-5-azabicyclo[2.2.1]heptan-5-ylmethyl]-8-oxa-3,5,10-triazatricyclo[7.4.0.0$^{2,7}$]trideca-1(13),2(7),3,5,9,11-hexaene

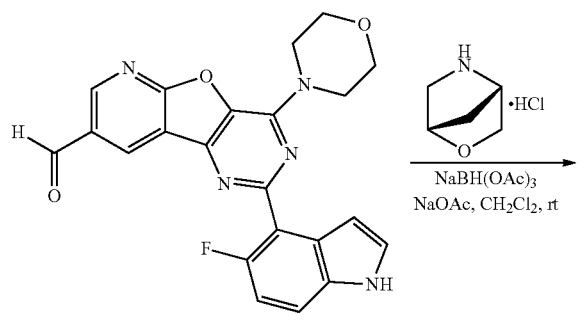

Intermediate 8

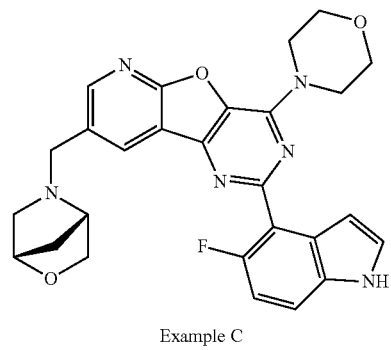

Example C

To a suspension of Intermediate 8 (50 mg, 0.12 mmol, 1 eq), (1S,4S)-2-oxa-5-azabicyclo[2.2.1]heptane hydrochloride (49 mg, 0.36 mmol, 3 eq) and NaOAc (30 mg, 0.36 mmol, 3 eq) in anhydrous CH$_2$Cl$_2$ (5 mL) was added NaBH(OAc)$_3$ (51 mg, 0.24 mmol, 2 eq). The reaction mixture was stirred at rt overnight. It had not reached completion, thus more reagents were added: (1S,4S)-2-oxa-5-azabicyclo[2.2.1]heptane hydrochloride (18 mg, 0.12 mmol, 1 eq) and NaOAc (10 mg, 0.12 mmol, 1 eq). The mixture was left to stir at rt overnight. Then, it was partitioned with H$_2$O (10 mL) and extracted with CH$_2$Cl$_2$ (3×10 mL). The combined organic extracts were dried over MgSO$_4$ and the solvent was removed by evaporation in vacuo. The residue was dissolved in CH$_2$Cl$_2$/MeOH (1:1, 20 mL) and swirled with MP-TMT resin (300 mg, 5 eq) overnight. The resin was then filtered off, washed with CH$_2$Cl$_2$/MeOH (1:1, 20 mL) and the solvent was removed in vacuo. Purification by silica gel column chromatography with EtOAc/MeOH (1:0-6:1) yielded Example C as a white solid (39.1 mg, 65%).

$^1$H NMR (300 MHz, CDCl$_3$) δ$_H$: 8.65 (d, J=2.3 Hz, 1H), 8.58 (d, J=2.1 Hz, 1H), 8.35 (br s, 1H), 7.37-7.45 (m, 1H), 7.33 (t, J=2.8 Hz, 1H), 7.08 (dd, J=10.9, 8.9 Hz, 1H), 6.95 (t, J=2.2 Hz, 1H), 4.45 (s, 1H), 4.19-4.27 (m, 4H), 4.16 (d, J=7.9 Hz, 1H), 3.97 (d, J=1.7 Hz, 2H), 3.85-3.94 (m, 4H), 3.68 (dd, J=7.9, 1.5 Hz, 1H), 3.52 (s, 1H), 2.93 (dd, J=10.1, 1.4 Hz, 1H), 2.60 (d, J=10.0 Hz, 1H), 1.94 (dd, J=9.6, 1.5 Hz, 1H), 1.78 (d, J=9.8 Hz, 1H).

MS (ES$^+$) 500.9 (100%, [M+H]$^+$).

Example D 4-(5-Fluoro-1H-indol-4-yl)-6-(morpholin-4-yl)-12-{2-oxa-7-azaspiro[3.5]nonan-7-ylmethyl}-8-oxa-3,5,10-triazatricyclo[7.4.0.0$^{2,7}$]trideca-1(13),2(7),3,5,9,11-hexaene

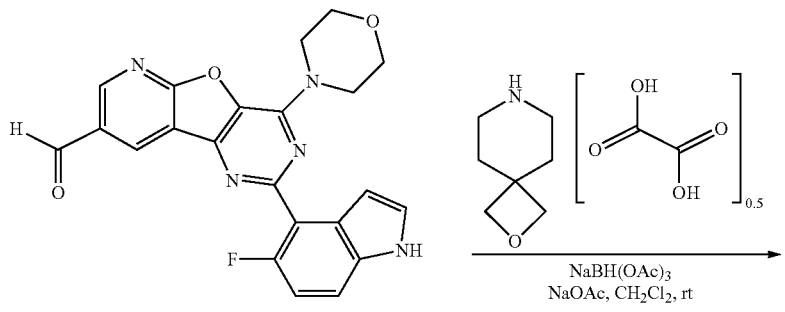

Intermediate 8

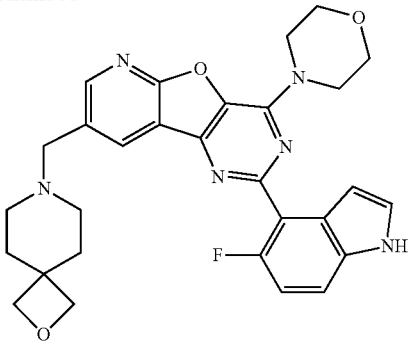

Example D

To a suspension of Intermediate 8 (50 mg, 0.12 mmol, 1 eq), 2-oxa-7-azaspiro[3.5]nonane hemioxalate (62 mg, 0.36 mmol, 3 eq) and NaOAc (30 mg, 0.36 mmol, 3 eq) in anhydrous CH$_2$Cl$_2$ (5 mL) was added NaBH(OAc)$_3$ (51 mg, 0.24 mmol, 2 eq). The reaction mixture was stirred at rt overnight. It had not reached completion, thus more reagents were added: 2-oxa-7-azaspiro[3.5]nonane hemioxalate (10 mg, 0.06 mmol, 1 eq) and NaOAc (5 mg, 0.06 mmol, 1 eq). The mixture was left to stir at rt overnight. Then, it was partitioned with H$_2$O (10 mL) and extracted with CH$_2$Cl$_2$ (3×10 mL). The combined organic extracts were dried over MgSO$_4$ and the solvent was removed by evaporation in vacuo. The residue was dissolved in CH$_2$Cl$_2$/MeOH (1:1, 20 mL) and swirled with MP-TMT resin (300 mg, 5 eq) overnight. The resin was then filtered off, washed with CH$_2$Cl$_2$/MeOH (1:1, 20 mL) and the solvent was removed by evaporation in vacuo. Purification by silica gel column chromatography with EtOAc/MeOH (1:0-6:1) yielded Example D as a white solid (38.8 mg, 61%).

$^1$H NMR (300 MHz, CDCl$_3$) δ$_H$: 8.59 (d, J=2.1 Hz, 1H), 8.53 (d, J=2.1 Hz, 1H), 8.35 (br s, 1H), 7.41 (dd, J=8.8, 3.9 Hz, 1H), 7.33 (t, J=2.8 Hz, 1H), 7.08 (dd, J=10.9, 8.9 Hz, 1H), 6.95 (t, J=2.2 Hz, 1H), 4.41 (s, 4H), 4.18-4.26 (m, 4H), 3.86-3.95 (m, 4H), 3.65 (s, 2H), 2.38 (br s, 4H), 1.84-1.92 (m, 4H).

MS (ES$^+$) 528.9 (100%, [M+H]+).

Example E 4-(5-Fluoro-1H-indol-4-yl)-12-[(3-methoxyazetidin-1-yl)methyl]-6-(morpholin-4-yl)-8-oxa-3,5,10-triazatricyclo[7.4.0.0$^{2,7}$]trideca-1(13),2(7),3,5,9,11-hexaene

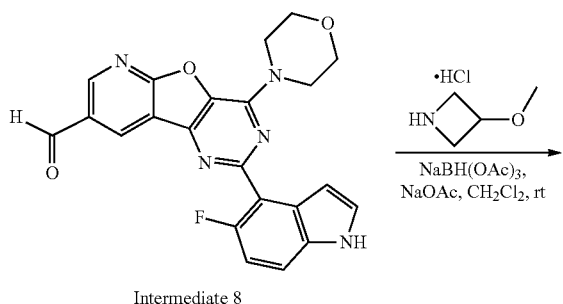

Intermediate 8

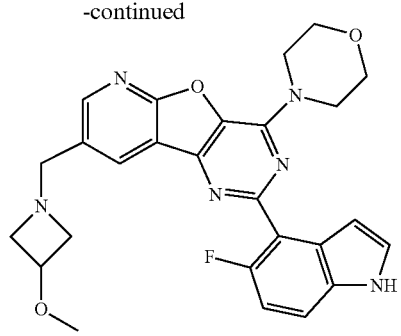

Example E

To a suspension of Intermediate 8 (50 mg, 0.12 mmol, 1 eq), 3-methoxyazetidine hydrochloride (44 mg, 0.36 mmol, 3 eq) and NaOAc (29 mg, 0.36 mmol, 3 eq) in anhydrous CH$_2$Cl$_2$ (8 mL) was added NaBH(OAc)$_3$ (51 mg, 0.24 mmol, 2 eq). The reaction mixture was stirred at rt for 22 h whereupon 1M NaOH (10 mL) and CH$_2$Cl$_2$ (5 mL) were added. The phases were separated and the aqueous phase re-extracted with CH$_2$Cl$_2$ (2×5 mL). The combined organic phases were washed with 50% brine (5 mL), dried (MgSO$_4$), and concentrated by evaporation in vacuo. The residue was dissolved in CH$_2$Cl$_2$/MeOH (1:1, 15 mL) and agitated with MP-TMT resin (300 mg, 0.68 mmol/g, 5 eq) overnight. The resin was then filtered off, washed with CH$_2$Cl$_2$/MeOH (1:1, 20 mL) and the solvent was removed by evaporation in vacuo. Purification by silica gel column chromatography eluting with EtOAc/MeOH (1:0-6:1) yielded Example E as a white solid (41 mg, 70%).

$^1$H NMR (300 MHz, CDCl$_3$) δ$_H$: 8.57 (d, J=2.2 Hz, 1H), 8.55 (d, J=2.2 Hz, 1H), 8.39 (br s, 1H), 7.41 (ddd, J=8.8, 3.9, 0.8 Hz, 1H), 7.29-7.35 (m, 1H), 7.08 (dd, J=10.9, 8.9 Hz, 1H), 6.92-6.99 (m, 1H), 4.17-4.27 (m, 4H), 4.10 (quin, J=5.7 Hz, 1H), 3.84-3.95 (m, 6H), 3.69-3.78 (m, 2H), 3.27 (s, 3H), 3.05-3.14 (m, 2H).

MS (ES$^+$) 489 (100%, [M+H]+).

Example F 6-(Morpholin-4-yl)-12-[(1S,4S)-2-oxa-5-azabicyclo[2.2.1]heptan-5-ylmethyl]-4-[2-(trifluoromethyl)-1H-indol-4-yl]-8-oxa-3,5,10-triazatricyclo[7.4.0.0$^{2,7}$]trideca-1(13),2(7),3,5,9,11-hexaene

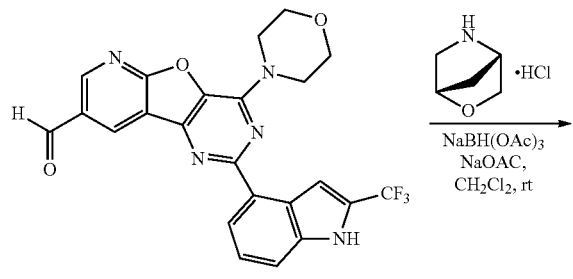

Intermediate 9

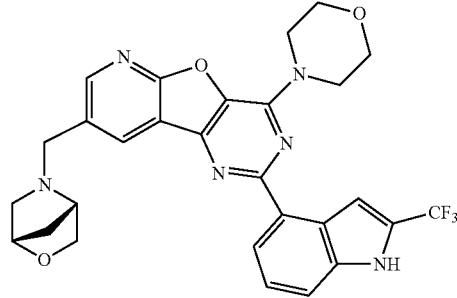

Example F

To a suspension of Intermediate 9 (50 mg, 0.11 mmol, 1 eq), (1S,4S)-2-oxa-5-azabicyclo[2.2.1]heptane hydrochloride (44 mg, 0.32 mmol, 3 eq) and NaOAc (26 mg, 0.36 mmol, 3 eq) in anhydrous $CH_2Cl_2$ (5 mL) was added $NaBH(OAc)_3$ (46 mg, 0.21 mmol, 2 eq). The reaction mixture was stirred at rt overnight. It had not reached completion, thus more reagents were added: (1S,4S)-2-oxa-5-azabicyclo[2.2.1]heptane hydrochloride (15 mg, 0.11 mmol, 1 eq) and NaOAc (9 mg, 0.11 mmol, 1 eq). The mixture was left to stir at rt overnight. Then, it was partitioned with $H_2O$ (10 mL) and extracted with $CH_2Cl_2$ (3×10 mL). The combined organic extracts were dried over $MgSO_4$ and the solvent was removed by evaporation in vacuo. The residue was dissolved in $CH_2Cl_2$/MeOH (1:1, 20 mL) and swirled with MP-TMT resin (300 mg, 5 eq) overnight. The resin was then filtered off, washed with $CH_2Cl_2$/MeOH (1:1, 20 mL) and the solvent was removed by evaporation in vacuo. Purification by silica gel column chromatography with EtOAc/MeOH (1:0-4:1) yielded Example F as a pale yellow solid (49.1 mg, 83%).

$^1$H NMR (300 MHz, $CDCl_3$) $\delta_H$: 8.68 (br s, 1H), 8.62-8.64 (m, 1H), 8.58-8.61 (m, 1H), 8.28 (dd, J=7.3, 0.9 Hz, 1H), 8.01-8.06 (m, 1H), 7.42-7.59 (m, 2H), 4.44-4.51 (m, 1H), 4.22-4.30 (m, 4H), 4.20 (d, J=7.9 Hz, 1H), 4.01 (d, J=2.1 Hz, 2H), 3.90-3.98 (m, 4H), 3.71 (dd, J=7.9, 1.7 Hz, 1H), 3.53-3.60 (m, 1H), 2.96 (dd, J=10.1, 1.6 Hz, 1H), 2.66 (d, J=10.2 Hz, 1H), 1.98 (dd, J=9.7, 1.6 Hz, 1H), 1.77-1.86 (m, 1H).

MS (ES$^+$) 551.2 (100%, [M+H]$^+$).

Example G 6-(Morpholin-4-yl)-12-({2-oxa-7-azaspiro[3.5]nonan-7-yl}methyl)-4-[2-(trifluoromethyl)-1H-indol-4-yl]-8-oxa-3,5,10-triazatricyclo[7.4.0.0$^{2,7}$]trideca-1(13),2(7),3,5,9,11-hexaene

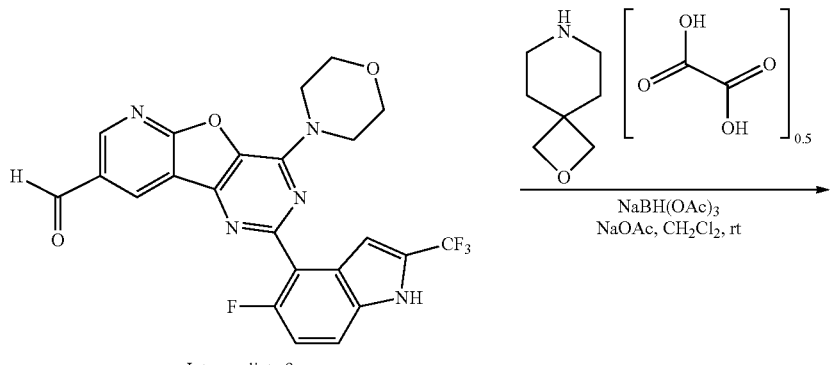

Intermediate 9

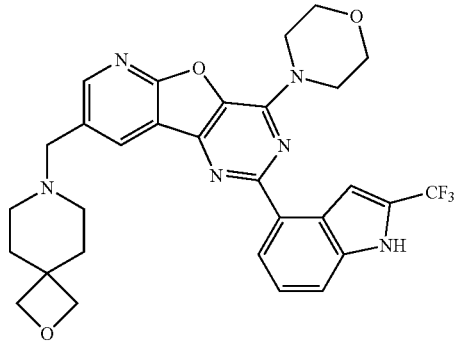

Example G

To a suspension of Intermediate 9 (50 mg, 0.11 mmol, 1 eq), 2-oxa-7-azaspiro[3.5]nonane hemioxalate (55 mg, 0.32 mmol, 3 eq) and NaOAc (26 mg, 0.32 mmol, 3 eq) in anhydrous CH$_2$Cl$_2$ (5 mL) was added NaBH(OAc)$_3$ (45 mg, 0.21 mmol, 2 eq). The reaction mixture was stirred at rt over 3 days. Each day, more reagents were added: 2-oxa-7-azaspiro[3.5]nonane hemioxalate (10 mg, 0.06 mmol, 1 eq) and NaOAc (5 mg, 0.06 mmol, 1 eq), as it had not reached completion. Then, it was partitioned with H$_2$O (10 mL) and extracted with CH$_2$Cl$_2$ (3×10 mL). The combined organic extracts were dried over MgSO$_4$ and the solvent was removed by evaporation in vacuo. The residue was dissolved in CH$_2$Cl$_2$/MeOH (1:1, 20 mL) and swirled with MP-TMT resin (300 mg, 5 eq) overnight. The resin was then filtered off, washed with CH$_2$Cl$_2$/MeOH (1:1, 20 mL) and the solvent was removed by evaporation in vacuo. Purification by silica gel column chromatography with EtOAc/MeOH (1:0-4:1) yielded Example G as a white solid (49.0 mg, 79%).

$^1$H NMR (300 MHz, CDCl$_3$) $\delta_H$: 8.69 (br s, 1H), 8.56-8.59 (m, 1H), 8.52-8.56 (m, 1H), 8.28 (dd, J=7.3, 1.1 Hz, 1H), 8.01-8.07 (m, 1H), 7.52-7.58 (m, 1H), 7.42-7.50 (m, 1H), 4.44 (s, 4H), 4.22-4.29 (m, 4H), 3.91-3.98 (m, 4H), 3.68 (s, 2H), 2.42 (br s, 4H), 1.92 (t, J=5.2 Hz, 4H).

MS (ES$^+$) 579.2 (100%, [M+H]$^+$).

Example H

12-[(3-Methoxyazetidin-1-yl)methyl]-6-(morpholin-4-yl)-4-[2-(trifluoromethyl)-1H-indol-4-yl]-8-oxa-3,5,10-triazatricyclo[7.4.0.0$^{2,7}$]trideca-1(13),2(7),3,5,9,11-hexaene

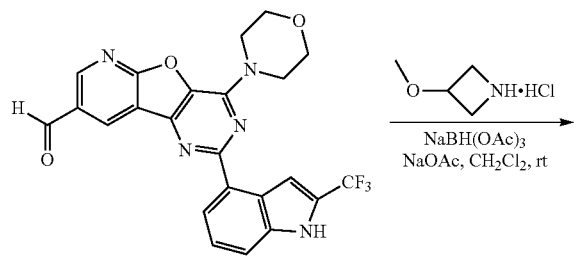
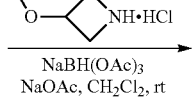

Intermediate 9

Example H

To a suspension of Intermediate 9 (49.5 mg, 0.11 mmol, 1 eq), 3-methoxyazetidine hydrochloride (26.2 mg, 0.21 mmol, 2 eq) and NaOAc (17.4 mg, 0.21 mmol, 2 eq) in anhydrous CH$_2$Cl$_2$ (7 mL) was added NaBH(OAc)$_3$ (45 mg, 0.21 mmol, 2 eq). The reaction mixture was stirred at rt for 3 h. The mixture was then re-charged with 3-methoxyazetidine hydrochloride (18.1 mg, 0.10 mmol, 1 eq) and NaOAc (8.7 mg, 0.10 mmol, 1 eq). It was left to stir at rt overnight. Then, it was partitioned with 1N NaOH (10 mL) and H$_2$O (10 mL), and extracted with CH$_2$Cl$_2$ (3×15 mL). The combined organic extracts were dried over MgSO$_4$ and the solvent was removed in vacuo. The residue was dissolved in CH$_2$Cl$_2$/MeOH (4:1, 20 mL) and swirled with MP-TMT resin (150 mg, 1.1 mmol/g, 5 eq) overnight. The resin was then filtered off, washed with CH$_2$Cl$_2$/MeOH (4:1, 20 mL) and the solvent was removed by evaporation in vacuo. Purification by silica gel column chromatography with CH$_2$Cl$_2$/MeOH (1:0-9:1), then EtOAc/MeOH (1:0-9:1) and CH$_2$Cl$_2$/MeOH (9:1) yielded Example H as a white solid (24.1 mg, 43%).

$^1$H NMR (300 MHz, DMSO-d$_5$) $\delta_H$: 12.46 (br s, 1H), 8.51-8.60 (m, 2H), 8.23-8.34 (m, 1H), 8.00 (s, 1H), 7.64 (d, J=8.3 Hz, 1H), 7.39-7.51 (m, 1H), 4.13 (d, J=4.5 Hz, 4H), 3.94-4.07 (m, 1H), 3.80-3.93 (m, 6H), 3.53 (t, J=6.7 Hz, 2H), 3.29 (s, 3H), 2.97 (t, J=6.2 Hz, 2H).

MS (ES$^+$) 539.2 (100%, [M+H]$^+$).

Example I 4-(6-Fluoro-1H-indol-4-yl)-12-[(3-methoxyazetidin-1-yl)methyl]-6-(morpholin-4-yl)-8-oxa-3,5,10-triazatricyclo[7.4.0.0$^{2,7}$]trideca-1(13),2(7),3,5,9,11-hexaene

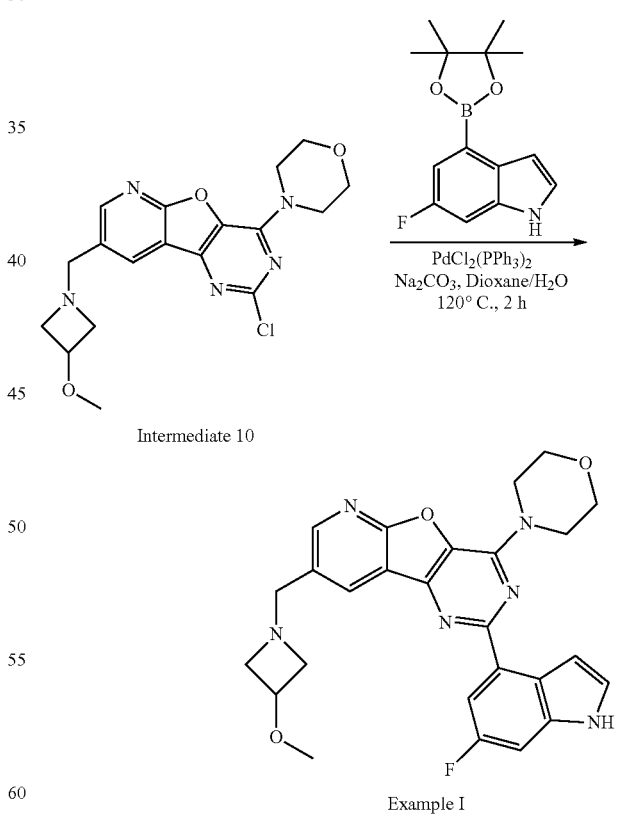

Intermediate 10

Example I

To Intermediate 10 (100 mg, 0.26 mmol, 1 eq) was added 6-fluoro-4-(tetramethyl-1,3,2-dioxaborolan-2-yl)-1H-indole (134 mg, 0.51 mmol, 2 eq), PdCl$_2$(PPh$_3$)$_2$ (36 mg, 0.051 mmol, 0.2 eq) and sodium carbonate (54 mg, 0.51 mmol, 2 eq) in dioxane (2.5 mL)/water (0.5 mL). The reaction mixture was heated in the microwave at 120° C. for 2 h. It was then cooled down to rt, partitioned with water (15 mL) and brine (20 mL), and extracted with CH$_2$Cl$_2$ (3×15 mL). The combined organics were dried over MgSO$_4$, filtered and the solvent was removed by evaporation in vacuo. The residue was dissolved in CH$_2$Cl$_2$/MeOH (4:1, 10 mL) and swirled with MP-TMT resin (~230 mg, 1.1 mmol/g, 5 eq) for 5 h. Upon filtration, the solvent was removed by evaporation in vacuo. Purification by silica gel column chromatography with EtOAc/MeOH (1:0-19:1) yielded Example I as an off-white solid (69 mg, 55%).

$^1$H NMR (300 MHz, DMSO-d$_5$) δ$_H$: 11.34 (br s, 1H), 8.59 (d, J=2.1 Hz, 1H), 8.56 (d, J=2.1 Hz, 1H), 7.96 (dd, J=11.6, 2.4 Hz, 1H), 7.52-7.58 (m, 1H), 7.47-7.52 (m, 1H), 7.34 (dd, J=9.2, 1.7 Hz, 1H), 4.12 (d, J=4.5 Hz, 4H), 4.01 (quin, J=5.7 Hz, 1H), 3.87 (d, J=4.7 Hz, 4H), 3.82 (s, 2H), 3.48-3.57 (m, 2H), 3.16 (s, 3H), 2.96 (dd, J=7.9, 5.8 Hz, 2H).

MS (ES$^+$) 489.0 (100%, [M+H]$^+$).

Example J 4-(6-Fluoro-1H-indol-4-yl)-12-[(3-methoxyazetidin-1-yl)methyl]-6-(morpholin-4-yl)-8-thia-3,5,10-triazatricyclo[7.4.0.0$^{2,7}$]trideca-1(13),2(7),3,5,9,11-hexaene

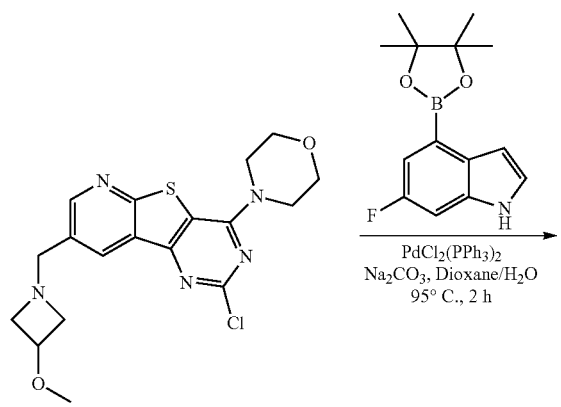

Intermediate 17

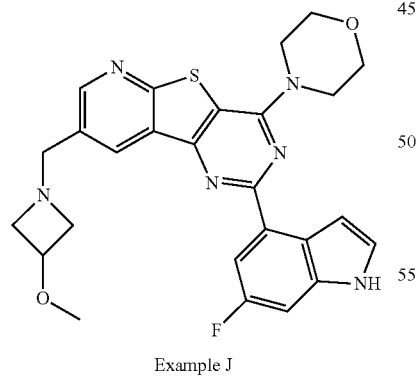

Example J

To Intermediate 17 (62 mg, 0.15 mmol, 1 eq) was added 6-fluoro-4-(tetramethyl-1,3,2-dioxaborolan-2-yl)-1H-indole (80 mg, 0.31 mmol, 2 eq), PdCl$_2$(PPh$_3$)$_2$ (22 mg, 0.031 mmol, 0.2 eq) and sodium carbonate (33 mg, 0.31 mmol, 2 eq) in dioxane (1.2 mL)/water (0.3 mL). The reaction mixture was heated at 95° C. for 2 h until completion. It was then cooled down to rt, partitioned with water (15 mL) and brine (20 mL), and extracted with CH$_2$Cl$_2$ (3×15 mL). The combined organics were dried over MgSO$_4$, filtered and the solvent was removed by evaporation in vacuo. The residue was dissolved in CH$_2$Cl$_2$/MeOH (4:1, 10 mL) and swirled with MP-TMT resin (~140 mg, 1.1 mmol/g, 5 eq) overnight. Upon filtration, the solvent was removed by evaporation in vacuo. Purification by silica gel column chromatography with EtOAc/MeOH (1:0-4:1) yielded Example J as a pale yellow solid (47 mg, 61%).

$^1$H NMR (300 MHz, DMSO-d$_5$) δ$_H$: 11.38 (br s, 1H), 8.79 (d, J=1.9 Hz, 1H), 8.68 (d, J=1.9 Hz, 1H), 8.06 (dd, J=11.4, 2.4 Hz, 1H), 7.51-7.60 (m, 2H), 7.37 (dd, J=9.4, 1.9 Hz, 1H), 3.97-4.09 (m, 5H), 3.79-3.91 (m, 6H), 3.48-3.60 (m, 2H), 3.16 (s, 3H), 2.92-3.02 (m, 2H).

MS (ES$^+$) 505.0 (100%, [M+H]$^+$).

Example K 4-(5-Fluoro-1H-indol-4-yl)-12-[(3-methoxyazetidin-1-yl)methyl]-6-(morpholin-4-yl)-8-thia-3,5,10-triazatricyclo[7.4.0.0$^{2,7}$]trideca-1(13),2(7),3,5,9,11-hexaene

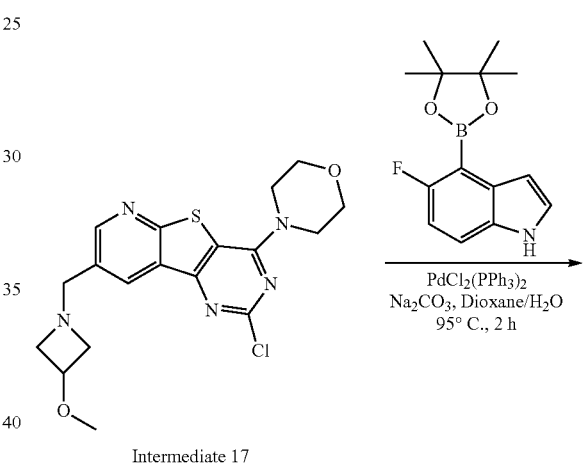

Intermediate 17

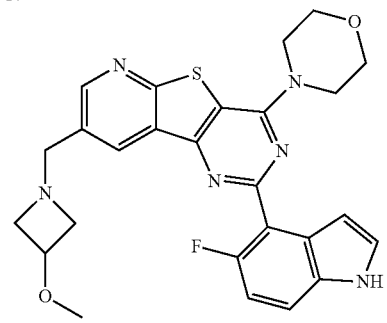

Example K

To Intermediate 17 (77.5 mg, 0.19 mmol, 1 eq) was added 5-fluoro-4-(tetramethyl-1,3,2-dioxaborolan-2-yl)-1H-indole (99.7 mg, 0.38 mmol, 2 eq), PdCl$_2$(PPh$_3$)$_2$ (27 mg, 0.038 mmol, 0.2 eq) and sodium carbonate (41 mg, 0.38 mmol, 2 eq) in dioxane (0.75 mL)/water (0.2 mL). The reaction mixture was heated in the microwave at 90° C. for 25 min. Upon completion, the solvent was removed by evaporation in vacuo. The residue was dissolved in CH$_2$Cl$_2$/MeOH (4:1, 5 mL) and swirled with MP-TMT resin (~150 mg, 1.1 mmol/g, 5 eq) overnight. Upon filtration, the solvent was removed by evaporation in vacuo. Purification by silica gel column chromatography with CH$_2$Cl$_2$/MeOH (1:0-9:1) then EtOAc/MeOH (1:0-9:1) yielded Example K as a white solid (61.0 mg, 63%).

$^1$H NMR (300 MHz, DMSO-d$_5$) δ$_H$: 11.32 (br s, 1H), 8.78 (d, J=2.1 Hz, 1H), 8.55 (d, J=2.1 Hz, 1H), 7.45-7.55 (m, 2H), 7.06 (dd, J=11.2, 8.8 Hz, 1H), 6.78-6.86 (m, 1H), 3.94-4.05 (m, 5H), 3.74-3.87 (m, 6H), 3.46-3.58 (m, 2H), 3.14 (s, 3H), 2.86-2.99 (m, 2H).

MS (ES$^+$) 505.2 (100%, [M+H]$^+$).

Example L

12-[(3-Methoxyazetidin-1-yl)methyl]-6-(morpholin-4-yl)-4-[6-(trifluoromethyl)-1H-indol-4-yl]-8-oxa-3,5,10-triazatricyclo[7.4.0.0$^{2,7}$]trideca-1(13),2(7),3,5,9,11-hexaene

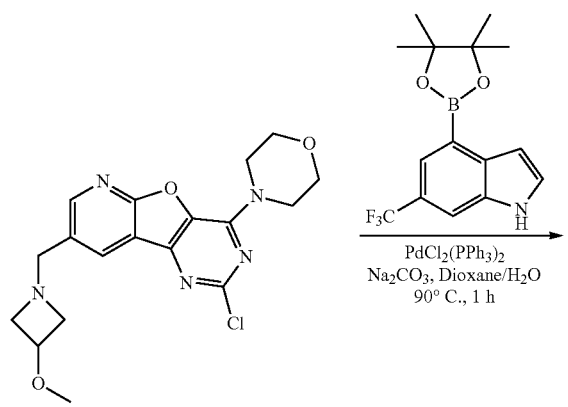

Intermediate 10

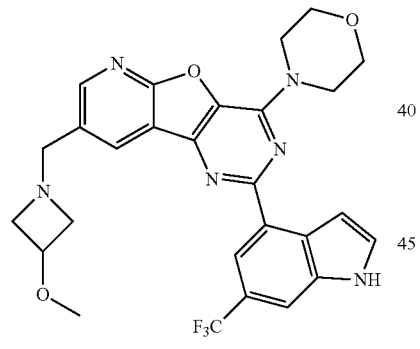

Example L

To Intermediate 10 (75 mg, 0.192 mmol, 1 eq) was added 4-(tetramethyl-1,3,2-dioxaborolan-2-yl)-6-(trifluoromethyl)-1H-indole (120 mg, 0.38 mmol, 2 eq), PdCl$_2$(PPh$_3$)$_2$ (27 mg, 0.038 mmol, 0.2 eq) and sodium carbonate (61 mg, 0.58 mmol, 3 eq) in dioxane (3 mL)/water (1 mL). The reaction mixture was heated at 90° C. for 1 h until completion. It was then cooled down to rt, partitioned with water (15 mL) and extracted with EtOAc (3×15 mL). The combined organics were dried over MgSO$_4$, filtered and the solvent was removed in vacuo. The residue was dissolved in CH$_2$Cl$_2$/MeOH (1:1, 10 mL) and swirled with MP-TMT resin (~250 mg, 1.1 mmol/g, 5 eq) overnight. Upon filtration, the solvent was removed by evaporation in vacuo. Purification by silica gel column chromatography with EtOAc/MeOH (1:0-9:1) yielded Example L as a pale yellow solid (59.8 mg, 58%).

$^1$H NMR (300 MHz, DMSO-d$_5$) δ$_H$: 11.73 (br s, 1H), 8.60 (d, J=1.7 Hz, 1H), 8.56 (d, J=1.9 Hz, 1H), 8.39-8.45 (m, 1H), 7.85-7.92 (m, 1H), 7.76 (t, J=2.5 Hz, 1H), 7.57-7.65 (m, 1H), 4.07-4.18 (m, 4H), 4.00 (quin, J=5.7 Hz, 1H), 3.84-3.92 (m, 4H), 3.81 (s, 2H), 3.47-3.57 (m, 2H), 3.15 (s, 3H), 2.96 (t, J=6.7 Hz, 2H).

MS (ES$^+$) 539.2 (100%, [M+H]$^+$).

Example M

12-[(3-Methoxyazetidin-1-yl)methyl]-6-(morpholin-4-yl)-4-[6-(trifluoromethyl)-1H-indol-4-yl]-8-thia-3,5,10-triazatricyclo[7.4.0.0$^{2,7}$]trideca-1(13),2(7),3,5,9,11-hexaene

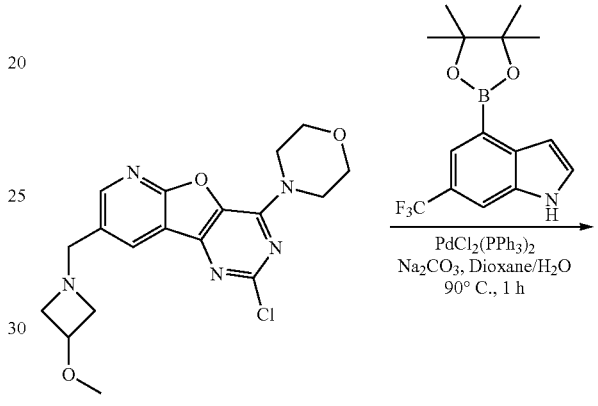

Intermediate 17

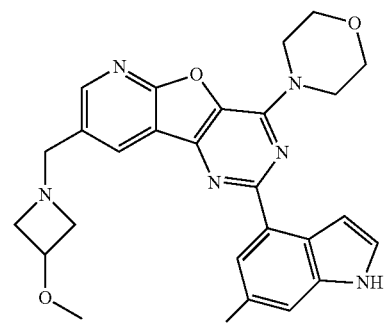

Example M

To Intermediate 17 (75 mg, 0.185 mmol, 1 eq) was added 4-(tetramethyl-1,3,2-dioxaborolan-2-yl)-6-(trifluoromethyl)-1H-indole (115 mg, 0.37 mmol, 2 eq), PdCl$_2$(PPh$_3$)$_2$ (26 mg, 0.037 mmol, 0.2 eq) and sodium carbonate (59 mg, 0.58 mmol, 3 eq) in dioxane (3 mL)/water (0.7 mL). The reaction mixture was heated at 90° C. for 1 h until completion. It was then cooled down to rt, partitioned with water (15 mL) and extracted with EtOAc (3×15 mL). The combined organics were dried over MgSO$_4$, filtered and the solvent was removed by evaporation in vacuo. The residue was dissolved in CH$_2$Cl$_2$/MeOH (1:1, 10 mL) and swirled with MP-TMT resin (~250 mg, 1.1 mmol/g, 5 eq) overnight. Upon filtration, the solvent was removed by evaporation in vacuo. Purification by silica gel column chromatography with EtOAc/MeOH (1:0-9:1) yielded Example M as a pale yellow solid (40.3 mg, 39%).

$^1$H NMR (300 MHz, DMSO-d$_5$) δ$_H$: 11.77 (br s, 1H), 8.79 (d, J=2.1 Hz, 1H), 8.67 (d, J=2.1 Hz, 1H), 8.50 (d, J=1.1 Hz,

1H), 7.88-7.94 (m, 1H), 7.80 (t, J=2.7 Hz, 1H), 7.62-7.70 (m, 1H), 3.97-4.10 (m, 5H), 3.81-3.92 (m, 6H), 3.50-3.59 (m, 2H), 3.16 (s, 3H), 2.93-3.03 (m, 2H).

MS (ES$^+$) 554.9 (100%, [M]$^+$).

Example N 4-(7-Fluoro-1H-indol-4-yl)-12-[(3-methoxyazetidin-1-yl)methyl]-6-(morpholin-4-yl)-8-oxa-3,5,10-triazatricyclo[7.4.0.0$^{2,7}$]trideca-1(13),2(7),3,5,9,11-hexaene

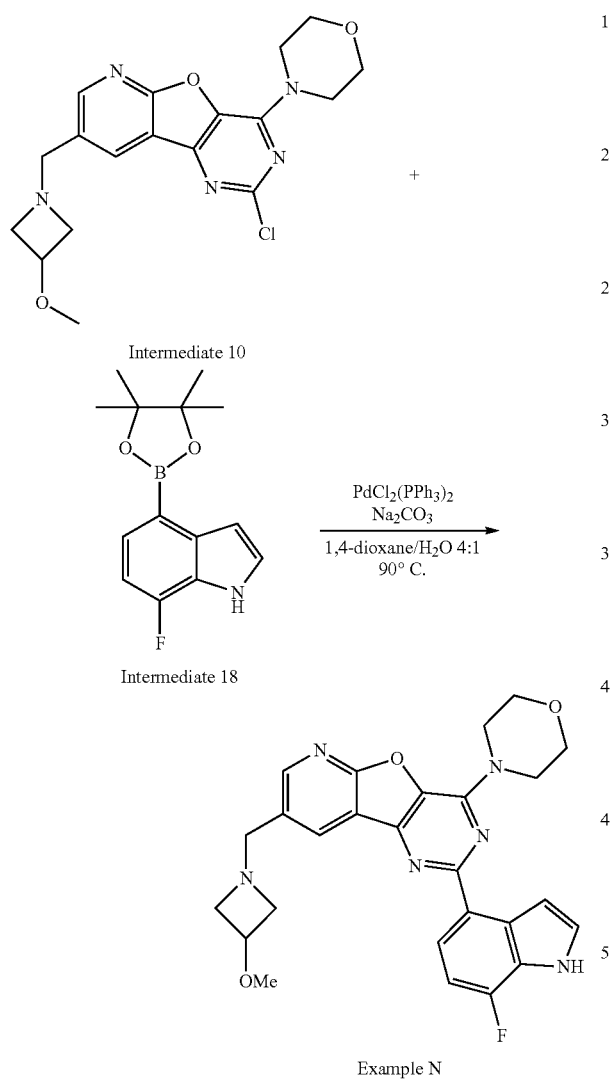

To a microwave vial containing Intermediate 10 (67.0 mg, 0.172 mmol, 1.0 eq), Intermediate 18 (89.8 mg, 0.344 mmol, 2.0 eq), sodium carbonate (36.5 mg, 0.344 mmol, 2.0 eq) and PdCl$_2$(PPh$_3$)$_2$ (24.1 mg, 0.0344 mmol, 20 mol %) were added 1,4-dioxane (0.7 mL) and H$_2$O (0.2 mL). The suspension was stirred at 90° C. for 3 h then cooled to rt. Additional portions of sodium carbonate (18.3 mg, 0.172 mmol, 1.0 eq) and PdCl$_2$(PPh$_3$)$_2$ (6.0 mg, 0.0086 mmol, 5 mol %) were added and the reaction was stirred at 90° C. for a further 1.5 h. Upon cooling, the mixture was diluted with H$_2$O (20 mL) and extracted with CH$_2$Cl$_2$ (3×25 mL). To the combined organic extracts were added MeOH (20 mL) and MP-TMT resin (400 mg, 0.440 mmol, 10 eq wrt Pd) and the mixture was swirled at rt for 17 h. The solution was filtered and the resin washed with CH$_2$Cl$_2$/MeOH (4:1, 100 mL). The filtrate was concentrated in vacuo and purified by silica gel column chromatography with CH$_2$Cl$_2$/EtOAc/MeOH (1:0:0-12:4:1) to yield Example N as an off-white solid (19.3 mg, 23%).

$^1$H NMR (300 MHz, DMSO-d$_6$) δ$_H$: 11.78 (br s, 1H), 8.47-8.63 (m, 2H), 8.17 (dd, J=8.3, 5.1 Hz, 1H), 7.59-7.67 (m, 1H), 7.55 (t, J=2.6 Hz, 1H), 7.06 (dd, J=10.7, 8.5 Hz, 1H), 4.07-4.21 (m, 4H), 4.00 (quin, J=5.7 Hz, 1H), 3.79-3.92 (m, 6H), 3.48-3.59 (m, 2H), 3.16 (s, 3H), 2.89-3.02 (m, 2H). $^{19}$F NMR (282 MHz, DMSO-d$_6$) δ$_F$: −131.08-−131.00 (m, 1F).

MS (ES$^+$) 489.0 (100%, [M+H]$^+$).

Example O 4-(5-Fluoro-1H-indol-4-yl)-6,12-bis(morpholin-4-yl)-8-oxa-3,5,10-triazatricyclo[7.4.0.0$^{2,7}$]trideca-1(9),2,4,6,10,12-hexaene

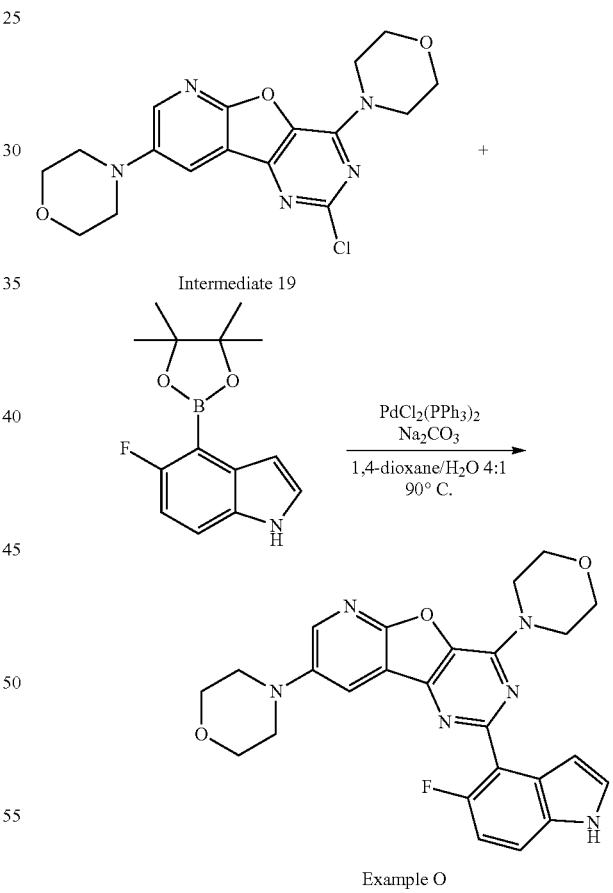

To a microwave vial containing Intermediate 19 (50.1 mg, 0.133 mmol, 1.0 eq), 5-fluoro-1H-indole-4-boronic acid pinacol ester (104 mg, 0.400 mmol, 3.0 eq), sodium carbonate (28.3 mg, 0.267 mmol, 2.0 eq) and PdCl$_2$(PPh$_3$)$_2$ (18.7 mg, 0.0267 mmol, 20 mol %) was added 1,4-dioxane (0.5 mL) and H$_2$O (0.1 mL). The suspension was stirred at 90° C. for 5 h then cooled to rt and re-charged with 5-fluoro-1H-indole-4-boronic acid pinacol ester (34.8 mg, 0.133 mmol, 1.0 eq), sodium carbonate (28.3 mg, 0.267 mmol, 2.0 eq), PdCl$_2$(PPh$_3$)$_2$ (9.4 mg, 0.0133 mmol, 210 mol %), 1,4-dioxane (0.4 mL) and H$_2$O (0.1 mL). The reaction mixture was then stirred at 90° C. for a further 16 h. After cooling to rt, the mixture was poured into H$_2$O (15 mL) and extracted with CH$_2$Cl$_2$ (3×15 mL). The combined organic extracts were dried over MgSO$_4$, filtered and concentrated in vacuo. The residue was re-dissolved in CH$_2$Cl$_2$/MeOH (4:1, 15 mL) and swirled with MP-TMT resin (350 mg, 0.385 mmol, 10 eq wrt Pd) at rt overnight. The solution was filtered, the resin washed with CH$_2$Cl$_2$/MeOH (4:1, 50 mL) and the filtrate concentrated in vacuo. Purification twice by silica gel column chromatography using CH$_2$Cl$_2$/MeOH (1:0-49:1) was followed by solid phase extraction using SCX-2, eluting with CH$_2$Cl$_2$/MeOH (1:0-0:1) then NH$_3$ in MeOH (0.1-0.5 M), yielding Example O as a yellow solid (30.0 mg, 48%).

$^1$H NMR (300 MHz, DMSO-d$_6$) $\delta_H$: 11.13-11.39 (m, 1H), 8.46 (d, J=3.0 Hz, 1H), 8.03 (d, J=3.0 Hz, 1H), 7.38-7.53 (m, 2H), 6.90-7.15 (m, 1H), 6.73 (t, J=2.1 Hz, 1H), 3.96-4.14 (m, 4H), 3.71-3.90 (m, 8H), 3.22-3.30 (m, 4H). $^{19}$F NMR (282 MHz, DMSO-d$_6$) $\delta_F$: −127.75--127.59 (m, 1F).

MS (ES$^+$) 475.1 (100%, [M+H]$^+$).

Example P

1-Ethyl-4-{[12-(5-fluoro-1H-indol-4-yl)-10-(morpholin-4-yl)-8-oxa-6-azatricyclo[7.4.0.0$^{2,7}$]trideca-1(9),2(7),3,5,10,12-hexaen-4-yl]methyl}piperazin-2-one

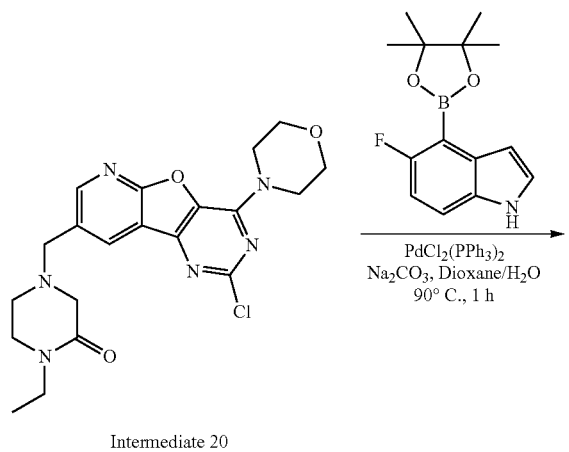

Intermediate 20

Example P

Under Ar, to Intermediate 20 (60 mg, 0.14 mol, 1 eq) was added 5-fluoro-4-(4,4,5,5-tetramethyl-1,3,2-dioxaborolan-2-yl)-1H-indole (73 mg, 0.28 mol, 2 eq), PdCl$_2$(PPh$_3$)$_2$ (20 mg, 0.03 mol, 0.2 eq) and sodium carbonate (30 mg, 0.28 mol, 2 eq) followed by dioxane (0.9 mL) and water (0.3 mL). The reaction mixture was heated at 90° C. overnight. The reaction mixture was cooled before CH$_2$Cl$_2$ (7 mL) and water (2 mL) were added. The phases were separated and the aqueous phase extracted with CH$_2$Cl$_2$ (2×2 mL). The combined organics were dried over MgSO$_4$, filtered and concentrated in vacuo. The resulting grey solid was dissolved in 1:1 CH$_2$Cl$_2$/MeOH (15 mL) then scavenged by addition of MP-TMT (125 mg, 0.71 mmol/g). The suspension was agitated overnight then filtered, washing the resin with 1:1 CH$_2$Cl$_2$/MeOH (2×10 mL) before concentrating the filtrate in vacuo. Purification by silica gel chromatography eluting with EtOAc/MeOH (1:0-9:1) yielded Example P (60 mg, 80%) as a white solid.

$^1$H NMR (300 MHz, DMSO-d$_6$) $\delta_H$: 11.29 (br s, 1H), 8.61 (d, J=2.3 Hz, 1H), 8.55 (d, J=2.1 Hz, 1H), 7.40-7.55 (m, 2H), 7.03 (dd, J=11.2, 8.8 Hz, 1H), 6.76 (t, J=2.2 Hz, 1H), 3.99-4.16 (m, 4H), 3.80-3.87 (m, 4H), 3.78 (s, 2H), 3.23-3.35 (m, 4H), 3.04 (s, 2H), 2.70 (br t, J=5.0 Hz, 2H), 1.01 (t, J=7.2 Hz, 3H). $^{19}$F NMR (282 MHz, DMSO-d$_6$) $\delta_F$: −127.53 (dd, J=10.8, 4.1 Hz, 1F).

MS (ES$^+$) 530.0 (100%, [M+H]$^+$)

Example Q 4-(3-Fluoro-1H-indol-4-yl)-12-[(3-methoxycyclobutyl)methyl]-6-(morpholin-4-yl)-8-oxa-3,5,10-triazatricyclo[7.4.0.0$^2$]trideca-1(13),2,4,6,9,11-hexaene

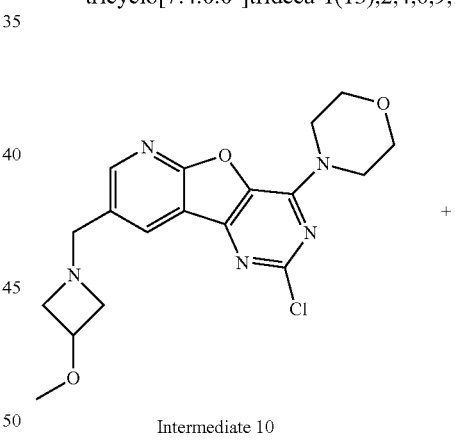

Intermediate 10

Intermediate 21

47

-continued

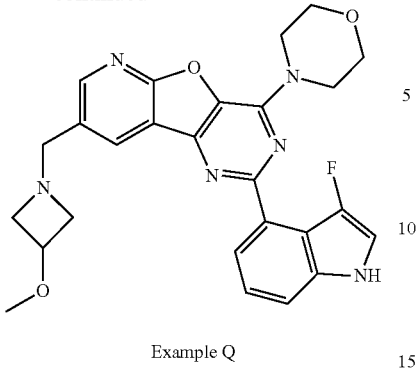

Example Q

To Intermediate 10 (67 mg, 0.17 mmol, 1 eq) was added Intermediate 21 (90 mg, 0.35 mmol, 2 eq), PdCl$_2$(PPh$_3$)$_2$ (24 mg, 0.035 mmol, 0.2 eq) and sodium carbonate (37 mg, 0.35 mmol, 2 eq), followed by dioxane-water (4:1, 1.7 mL). The reaction mixture was heated to 95° C. for 2 h. It was then cooled to rt and partitioned between CH$_2$Cl$_2$ (20 mL) and aqueous sodium chloride solution (12.5% w/w, 20 mL). The aqueous phase was re-extracted with CH$_2$Cl$_2$ (3×5 mL) and the combined organics were dried over MgSO$_4$, filtered and concentrated in vacuo. The filtrate was Pd-scavenged with MP-TMT resin (~156 mg, 1.1 mmol/g, 5 eq) overnight. The resin was removed by filtration and the filtrate was concentrated in vacuo. Purification The residue was purified by silica gel column chromatography using with EtOAc/MeOH (1:0-7:1) to afford the Example Q as an off-white solid (47 mg, 56%).

$^1$H-NMR (300 MHz, DMSO-d$_5$) δ$_H$: 11.06 (br s, 1H), 8.52-8.60 (m, 1H), 8.48 (d, J=1.3 Hz, 1H), 7.68 (d, J=7.3 Hz, 1H), 7.45-7.52 (m, 1H), 7.38-7.44 (m, 1H), 7.24 (t, J=7.9 Hz, 1H), 4.05-4.17 (m, 4H), 4.00 (quin, J=5.7 Hz, 1H), 3.76-3.88 (m, 6H), 3.47-3.57 (m, 2H), 3.15 (s, 3H), 2.96 (br s, 2H). $^{19}$F-NMR (DMSO-d$_5$) δ$_F$: -163.3 (m, 1H).

MS (ES$^+$) 489.0 (100%, [M+H]$^+$).

Example R 4-(3-Fluoro-1H-indol-4-yl)-12-[(3-methoxycyclobutyl)methyl]-6-(morpholin-4-yl)-8-thia-3,5,10-triazatricyclo[7.4.0.0$^2$]trideca-1(13),2,4,6,9,11-hexaene

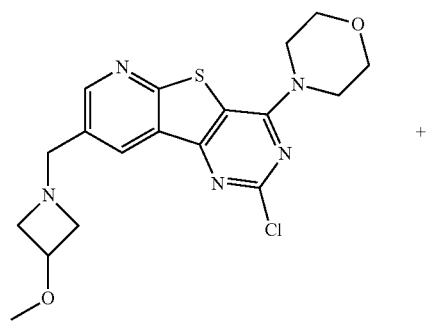

Intermediate 17

48

-continued

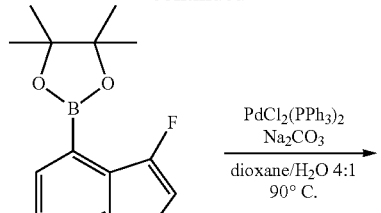

Intermediate 21

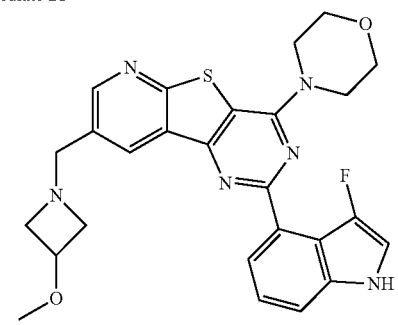

Example R

To Intermediate 17 (70 mg, 0.17 mmol, 1 eq) was added Intermediate 21 (90 mg, 0.35 mmol, 2 eq), PdCl$_2$(PPh$_3$)$_2$ (24 mg, 0.035 mol, 0.2 eq) and sodium carbonate (37 mg, 0.35 mmol, 2 eq), followed by 1,4-dioxane-water (4:1, 1.7 mL). The reaction mixture was heated to 95° C. for 2 h. It was then cooled to rt and partitioned between CH$_2$Cl$_2$ (20 mL) and aqueous sodium chloride solution (12.5% w/w, 20 mL). The aqueous phase was re-extracted with CH$_2$Cl$_2$ (3×5 mL) and the combined organics were dried over MgSO$_4$, filtered and concentrated in vacuo. The filtrate was Pd-scavenged with MP-TMT resin (~156 mg, 1.1 mmol/g, 5 eq) overnight. The resin was removed by filtration and the filtrate was concentrated in vacuo. Purification by silica gel column chromatography with EtOAc/MeOH (1:0-8:1) yielded Example R as a pale green solid (43 mg, 50%).

$^1$H NMR (300 MHz, DMSO-d$_5$) δ$_H$: 11.11 (br s, 1H), 8.77 (d, J=2.1 Hz, 1H), 8.59 (d, J=2.1 Hz, 1H), 7.80 (dd, J=7.3, 0.9 Hz, 1H), 7.51 (d, J=1.7 Hz, 1H), 7.45 (t, J=2.7 Hz, 1H), 7.23-7.31 (m, 1H), 3.95-4.09 (m, 5H), 3.71-3.91 (m, 6H), 3.47-3.58 (m, 2H), 3.10-3.18 (m, 3H), 2.89-2.99 (m, 2H). $^{19}$F NMR (282 MHz, DMSO-d$_5$) δ$_F$: -162.8 (m, 1H).

MS (ES$^+$) 505.0 (100%, [M+H]$^+$).

Biological Data

Fold isoform selectivity inhibition against class I PI3K isoforms, as confirmed following K$_i$ determination using the non-radiometric ADP-Glo™ assay (Promega, Madison, Wis., USA) at Proqinase GmbH is listed below.

| EXAMPLE | FOLD K$_i$ | | | |
|---|---|---|---|---|
| | p110β/p110α | p110β/p110γ | p110δ/p110α | p110β/p110γ |
| A | ** | ** | *** | *** |
| B | ** | ** | *** | *** |
| C | *** | *** | **** | **** |
| D | *** | *** | *** | *** |
| E | ** | *** | ** | **** |
| F | NT | NT | NT | NT |
| G | NT | NT | NT | NT |
| H | * | * | * | * |

-continued

| | FOLD $K_i$ | | | |
|---|---|---|---|---|
| EXAMPLE | p110β/p110α | p110β/p110γ | p110δ/p110α | p110β/p110γ |
| I | *** | *** | *** | *** |
| J | NT | NT | NT | NT |
| K | * | * | * | * |
| L | * | * | * | * |
| M | NT | NT | NT | NT |
| N | * | * | ** | ** |
| O | * | ** | * | ** |
| P | * | * | ** | ** |
| Q | ** | ** | ** | ** |
| R | NT | NT | NT | NT |

Key
* <10x
** ≥10x < 50x
*** ≥50x < 100x
**** ≥100x
NT: not tested

Rodent Pharmacokinetic Comparative Data

Disclosed compounds have improved pharmacokinetic parameters such as increased bioavailability and/or reduced clearance (data below for mice).

Example E

The following protocol was used to determine oral bioavailability and clearance.
The results are shown below.
Species=male mouse;
Strain=CD1,
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of pharmacokinetic parameters.
Formulation: 10% DMSO, 15% Cremophor, 75% Saline
Dosing: 10 mg/kg P.O. and 5 mg/kg I.V.
Plasma PK Summary:

| Parameters - IV, 5 mg/kg | Value - Free Base |
|---|---|
| $t_{1/2}$ (hr) | 0.55 |
| $T_{max}$ (hr) | 0.08 |
| $C_{max}$ (ng/mL) | 3621.10 |
| $AUC_{last}$ (hr*ng · mL) | 2934.93 |
| $AUC_{all}$ (hr*ng/mL) | 2934.93 |
| $AUC_{inf}$ (hr*ng/mL) | 3005.95 |
| Clearance (mL/hr/Kg) | 1663.37 |
| | (28 mL/min/Kg) |
| Vd (mL/Kg) | 1294.11 |

| Parameters - PO, 10 mg/kg | Value - Free Base |
|---|---|
| $t_{1/2}$ (hr) | 1.34 |
| $T_{max}$ (hr) | 0.50 |
| $C_{max}$ (ng/mL) | 1286.00 |
| $AUC_{last}$ (hr*ng/mL) | 2784.41 |
| $AUC_{all}$ (hr*ng/mL) | 2784.41 |
| $AUC_{inf}$ (hr* ng/mL) | 2827.00 |
| F | 47% |

Oral bioavailability (F)=47%
Clearance=28 mL/min/kg

Example I in WO 2011/021038—Mesylate Salt

The following protocol was used to determine oral bioavailability and clearance.
The results are shown below.
Species=male mouse;
Strain=CD1,
n=3 male mice per time point per route;
Terminal blood sampling at 8 time points (5 min, 10 min, 0.5 hr, 1 hr, 3 hr, 6 hr, 8 hr and, 24 hr);
Collection of plasma, bio-analysis and report of pharmacokinetic parameters.
Formulation: 10% DMSO, 90 & saline
Dosing: 10 mg/kg P.O. and 5 mg/kg I.V.

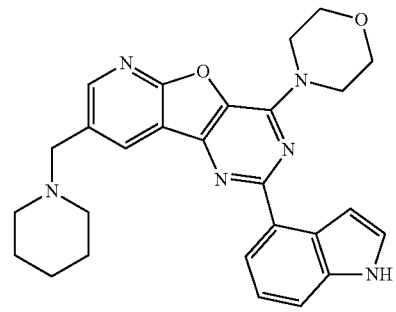 [SMILES: c1cc(-c2nc(N3CCOCC3)c3oc4ncc(CN5CCCCC5)cc4c3n2)c2cc[nH]c2c1]

Oral bioavailability=28%
Clearance=66 mL/min/kg

The invention claimed is:
1. A compound represented by:

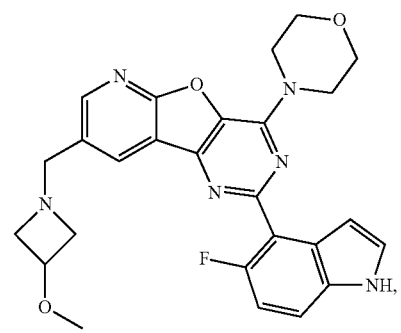 [SMILES: COC1CN(Cc2cnc3oc4c(N5CCOCC5)nc(-c5c(F)ccc6[nH]ccc56)nc4c3c2)C1]

or
a pharmaceutically acceptable salt thereof.
2. A pharmaceutical composition comprising a compound according to claim 1, and a pharmaceutically acceptable excipient.